United States Patent [19]
Gruber

[11] 4,435,984
[45] Mar. 13, 1984

[54] ULTRASONIC MULTIPLE-BEAM TECHNIQUE FOR DETECTING CRACKS IN BIMETALLIC OR COARSE-GRAINED MATERIALS

[75] Inventor: George J. Gruber, San Antonio, Tex.

[73] Assignee: Southwest Research Institute, San Antonio, Tex.

[21] Appl. No.: 268,145

[22] Filed: May 28, 1981

Related U.S. Application Data

[63] Continuation-in-part of Ser. No. 142,216, Apr. 21, 1980, Pat. No. 4,299,128.

[51] Int. Cl.$^3$ ............................................. G01N 29/04
[52] U.S. Cl. ..................................... 73/628; 73/1 DV
[58] Field of Search ................. 73/628, 620, 624, 625, 73/627, 629, 641, 597, 598, 589, 609, 1 DV

[56] References Cited

U.S. PATENT DOCUMENTS 3,683,680  8/1972  Johnson et al. ........................ 73/628
3,972,228  8/1976  Mansson ............................... 73/609

FOREIGN PATENT DOCUMENTS 2043899  10/1980  United Kingdom .................. 73/628

OTHER PUBLICATIONS

O. Ganglbauer et al., "Contributions to the Ultrasonic Testing of Austenitic Welds using Longitudinal Angle-Beam Probes", Ninth World Conference on Non-destructive Testing, pp. 1–6, Oct. 1979.
G. J. Gruber et al., "Reliability Evaluation of Six Ultrasonic Techniques for Cladded Pipe Examinations", *Proceedings of 11th Nuclear Power Ed. Sem.*, Apr. 20, 1981, pp. 1—35.
G. J. Gruber et al., "Detection of Surface Cracks in Bimetallic Coarse-Grained Structures", pp. 1-58, Dec. 1980.
R. J. Hudgell et al., "Ultrasonic Longitudinal Wave Examination of Austenitic Welds", *British Journal of NDT*, 22, pp. 78-85, Mar. 1980.
D. S. Kupperman et al., "Effects of Microstructure on Ultrasonic Examination of Stainless Steel", *Proceed. Cnsi. Spec. Meeting Ultra Insp. Reac. Comp.*, pp. 1–16, Sep. 1976.
D. S. Kupperman et al., "Effect of Shear Wave Polarization on Defect Detection in Stainless Steel Weld Metal", *Ultrasonics*, 16, pp. 21-27, Jan. 1978.
P. Caussin et al., "Factors Affecting Reliability Ultrasonic Exam. of Austenitic Components" *Proceed Cnsi. Spec. Meeting Ultra Insp. Reac. Comp.*, pp. 421–440, May 1980.
B. Trumpff et al., "Contribution Improving Ultrasonic Test of Thick Bimetallic Welds", *Proceed Cnsi. Spec. Meeting Ultra Insp. Reac. Comp.*, pp. 25–39, May 1980.
X. Edelmann, "Practical Application of Ultrasonic Testing of Austenitic Weld Joints", *Materials Evaluation*, pp. 47-51, Sep. 1979.
N. V. Vindogradov et al., "Dissipation of Ultrasonic Oscillations at Boundary Layers of Bimetal made by Explosive Welding", *Soviet Journal NDT*, 12, pp. 647-651, Dec. 1976.

*Primary Examiner*—Stephen A. Kreitman
*Attorney, Agent, or Firm*—Gunn, Lee & Jackson

[57] ABSTRACT

A reliable ultrasonic method for testing inner diameter cladded pipe adjacent to welds comprising use of multiple beams, bands and pulses in addition to pulseshaping and beamforming, spectral and directional averaging, as well as spatial filtering and pattern recognition. An automated inspection mode aims short shear-wave pulses from different source locations and different beam orientations to detect signals characteristic of defects. A manual confirmation mode aims both longitudinal waves and shear waves at the suspected defect and analyzes the detected returned pulses by an associated pulse pattern recognition method.

33 Claims, 20 Drawing Figures

$e_1$    $e_2$ $$SIR = \frac{(A_1 - A_0)^2}{\sigma^2}$$

PROBE B ALONE
CLADDED SPECIMEN

PROBE A ALONE
CLADDED SPECIMEN

PROBES A AND B
UNCLADDED SPECIMEN

PROBES A AND B
CLADDED SPECIMEN

ARRAY POS 9
UNCLADDED SPECIMEN

ARRAY POS 9
CLADDED SPECIMEN

ARRAY POS 3
UNCLADDED SPECIMEN

ARRAY POS 3
CLADDED SPECIMEN

ARRAY POS 6
UNCLADDED SPECIMEN

ARRAY POS 6
CLADDED SPECIMEN

ULTRASONIC MULTIPLE-BEAM TECHNIQUE FOR DETECTING CRACKS IN BIMETALLIC OR COARSE-GRAINED MATERIALS

CROSS-REFERENCES TO RELATED APPLICATIONS

This application is a continuation-in-part application of pending prior application Ser. No. 142,216 filed Apr. 21, 1980, now U.S. Pat. No. 4,299,128, by the same inventor for Ultrasonic Satellite-Pulse Technique For Characterizing Defects of Arbitrary Shape, which application is incorporated herein for all purposes.

BRIEF SUMMARY OF THE INVENTION

Inner-diameter cladding of pipe adjacent to welds to reduce susceptibility of the wrought structure to intergranular stress corrosion cracking leads to unexpected inspection difficulties. Since the spurious echoes ("interference") occupy a region of the time domain in which defect echoes ("signal") could be present, the examiner does not know which parts of a given waveform are relevant and which ones are not. There is no lack of indications. The main problem is, instead, the inability of the ultrasonic technique to discriminate against the false indications.

The main difficulties in the interpretation of test results were traced to the anisotropy and inhomogeneity of bimetallic coarse-grained structures. The reliability of the crack-detection process is limited by the various multiple refraction (beam skewing, widening, and narrowing) and backscattering (surface and volume reverberation) phenomena. Because of the deterministically indescribable dependence of sound velocity on the direction of propagation (anisotropy) and the local values of the elastic constants (inhomogeneity), the ultrasound is refracted and scattered in a statistical manner when propagating through a bimetallic coarse-grained structure. Refraction phenomena results mainly in reduced signal and missing the defect, and backscattering phenomena results mainly in increased background interference and false alarms. Because of the statistical aspects of wave propagation, it is not possible to specify crack detection criteria using signal amplitude alone.

The invented Multiple-Beam Technique (MBT) was developed especially for ultrasonic inservice inspection of the welds and heat-affected zones of cladded pipes. Use of the selected combination of compatible probes and operations as described herein leads to sufficiently reliable inspection results. Because the "optimum" values of the key ultrasonic parameters (beam angle, wave mode, center frequency, bandwidth, etc.) vary randomly with probe position on the surface of a bimetallic coarse-grained specimen, the use of multiple beams, bands, and pulses is proposed. In addition to pulseshaping and beamforming, spectral and directional averaging as well as spatial filtering and pattern recognition can be used to improve the ultrasonic inspectability of bimetallic coarse-grained structures.

Because of the existence of multiple preferred paths in bimetallic coarse-grained structures, two wave modes, three incident beams, and two receiver bands are employed in the MBT. The three beams overlap in a wide depth range and the same probe arrangement can be used over a wide specimen thickness range. Two modes of operation, an inspection mode and a confirmation mode, are combined to yield sufficiently reliable test results. In the automated inspection mode of operation of the MBT, two probes in a nonlinear array are used to transmit two short shear-wave pulses one after the other. The beams enter the base material at the approximate angles of 30 and 40 degrees, respectively. In the manual confirmation mode of operation of the MBT, one probe is used to transmit a short shear-wave pulse and a short longitudinal-wave pulse simultaneously. The beams enter the base material at the approximate angles of 30 and 70 degrees, respectively. The returned detected pulses are then analyzed by an associated pulse pattern recognition method to confirm the defects.

The use of two wideband probes, three overlapping incident beams, and four special operations performed on the received waveforms has produced acceptable test results.

BRIEF DESCRIPTION OF THE DRAWINGS

FIG. 1(a) shows the echoes generated by three sought-after defects ("signal").

FIG. 1(b) shows the general background echoes received from a defect-free speciman ("interference").

FIG. 1(c) shows the signal of FIG. 1(a) combined with the interference of FIG. 1(b). The ultrasonic tester's task is to locate as many of the defects contained in the interrogated volume as possible while false alarming as little as possible.

Figure 4:
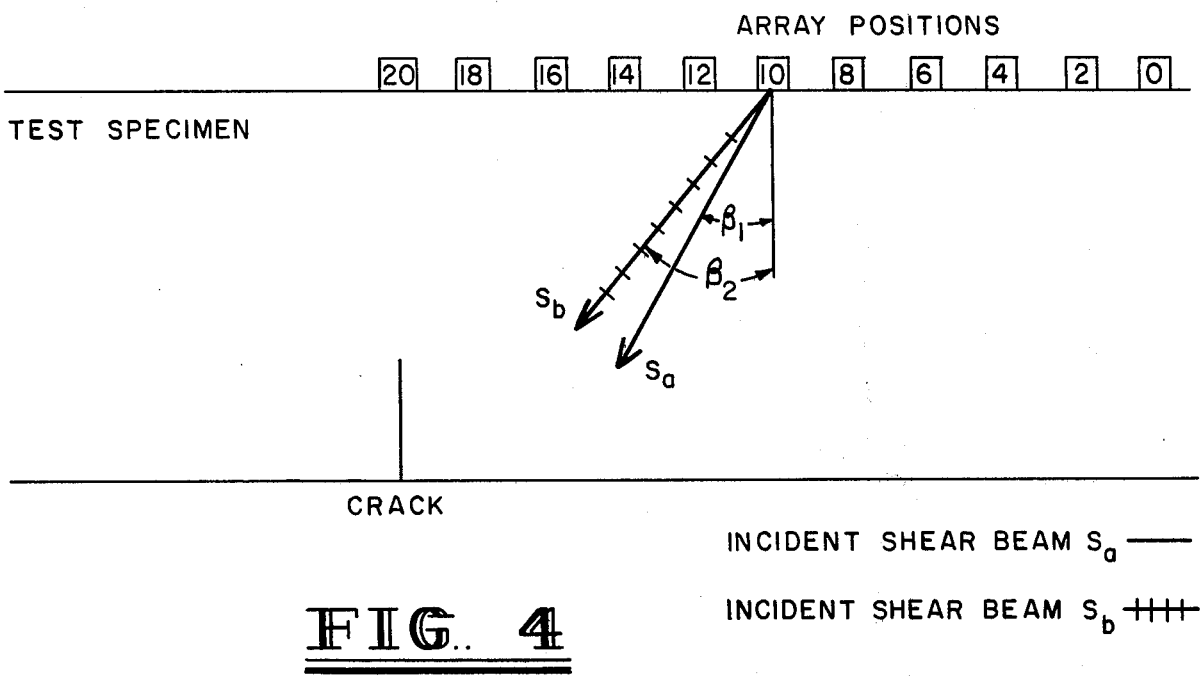
FIG. 4 shows various numbered array positions upon the examination surface of an uncladded test specimen with regard to an ultrasonic wave reflector such as a crack-like defect upon the far surface of the specimen. The $S_a$ and $S_b$ incident shear-wave beams are shown emanating from the array at array position 10. The angles $\beta_1$ and $\beta_2$ represent the directions of the incident shear beams with respect to a line perpendicular to the examination surface. This illustrates the Multiple-Beam Technique in its inspection mode (Mode I) as shown in FIG. 3.
Figure 5:
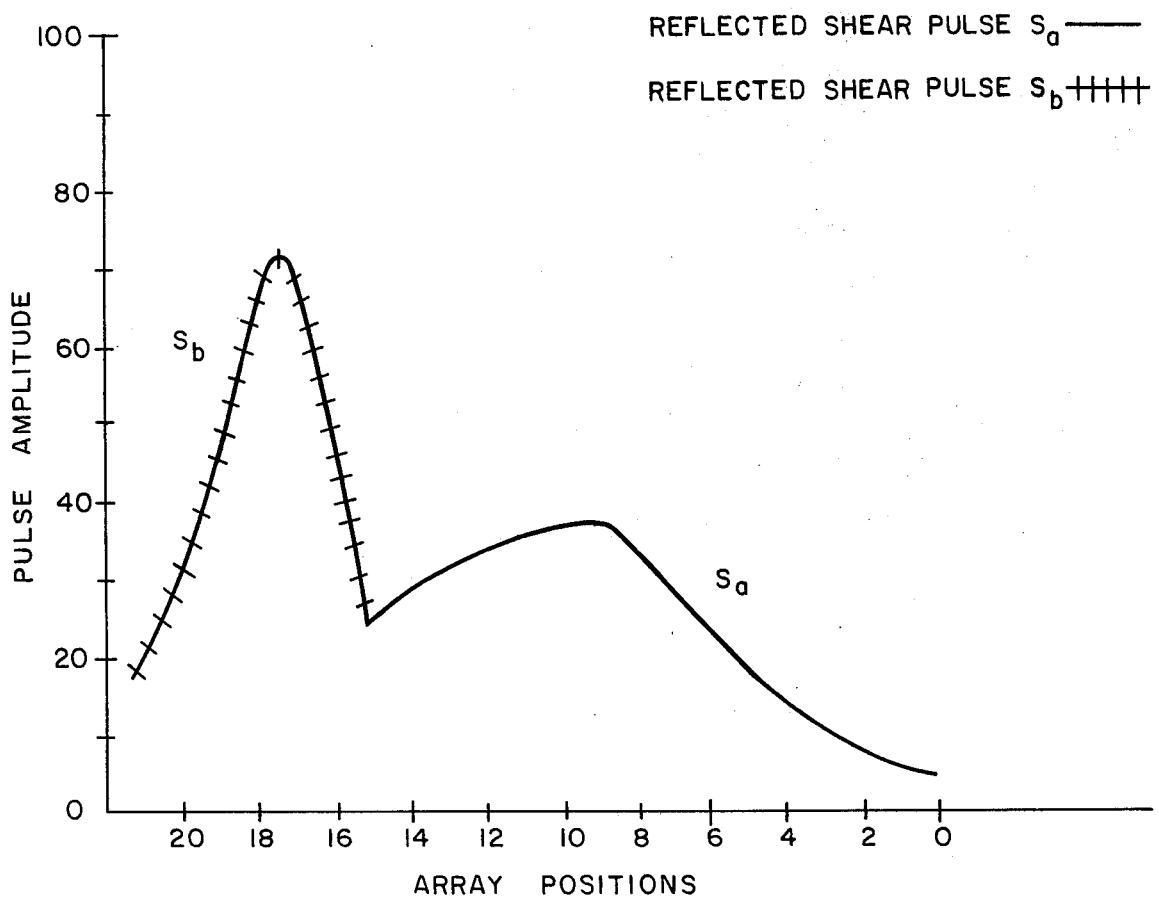
FIG. 5 shows the relative amplitudes of the $S_a$ and $S_b$ pulses reflected from a surface-connected crack insonified by the array as shown in FIG. 4. The array positions along the graph's horizontal axis correspond to the array positions shown in FIG. 4. The $S_b$ pulse is stronger than the $S_a$ pulse because, as shown in FIG. 3, the $\alpha_1$ angle is smaller for probe A than the $\alpha_2$ angle for probe B. The $S_b$ pulse is larger than the $S_a$ pulse because probe A transmits a longitudinal wave as well as a shear wave.

(a) shows a waveform received from a crack in a cladded test specimen when only probe B is used and the described array is positioned at array position 15 as shown in FIGS. 4 and 5.

(b) shows a waveform received from a crack in a cladded test specimen when only probe A is used and the described array is positioned at array position 15 as shown in FIGS. 4 and 5.

(c) shows a waveform received from a crack in an uncladded test specimen when probes A and B are connected electrically in parallel and the described array is positioned at array position 15 as shown in FIGS. 4 and 5.

(d) shows a waveform received from a crack in a cladded test specimen when both probe A and probe B are used in the described array and the array is positioned on the test specimen at array position 15 as shown in FIGS. 4 and 5.

Figure 7:
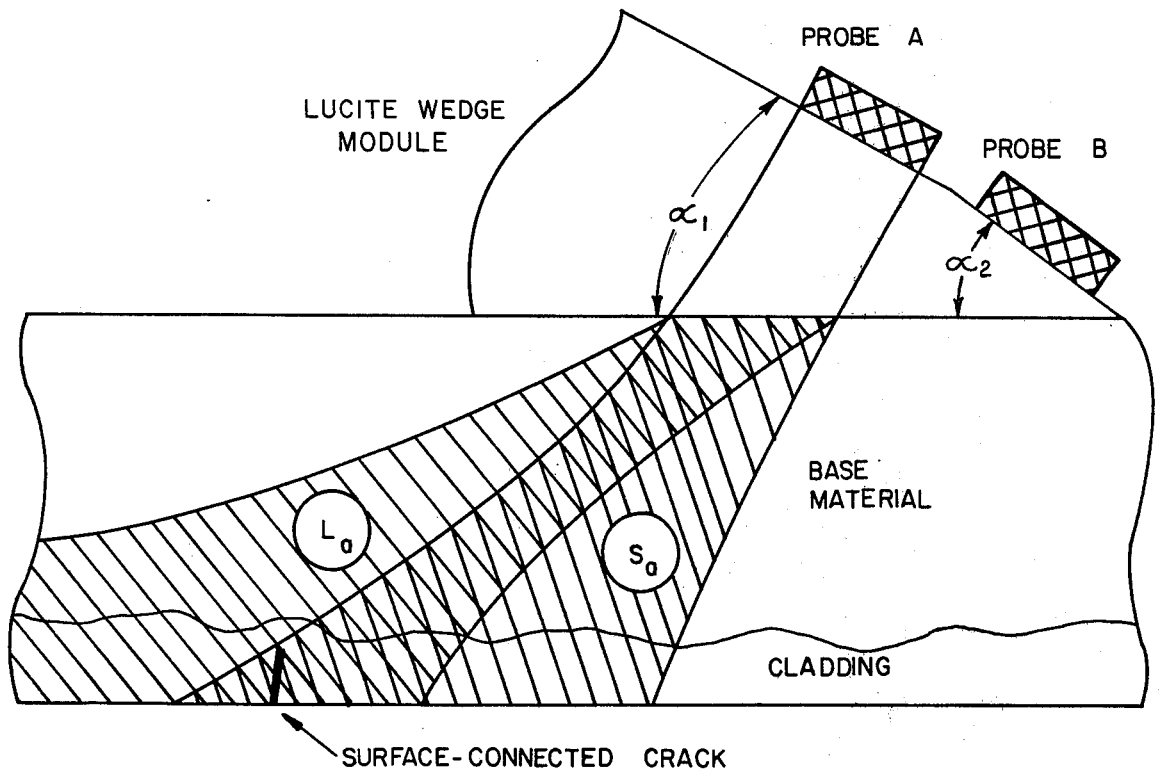

FIG. 7 shows the use of multiple beams in the call-confirmation mode (Mode II) of the Multiple-Beam Technique.

Figure 8:
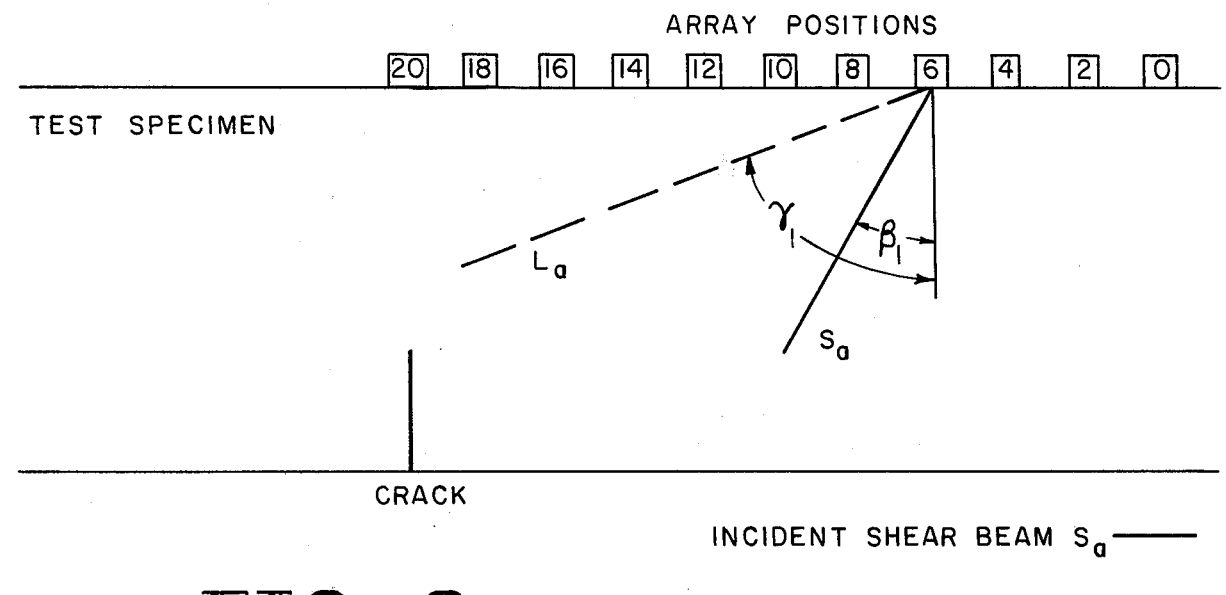

FIG. 8 shows various array positions upon the examination surface of an uncladded test specimen with regard to an ultrasonic wave reflector such as a crack-like defect upon the far surface of the test specimen. The $S_a$ and $L_a$ incident beams are shown emanating from the array at array position 6. The angle $\beta_1$ represents the direction of the incident shear beam with respect to a line perpendicular to the examination surface. The angle $gamma_1$ represents the direction of the incident longitudinal beam with respect to a line perpendicular to the examination surface. This illustrates use of the Multiple-Beam Technique in its call-confirmation mode (Mode II).

Figure 9:
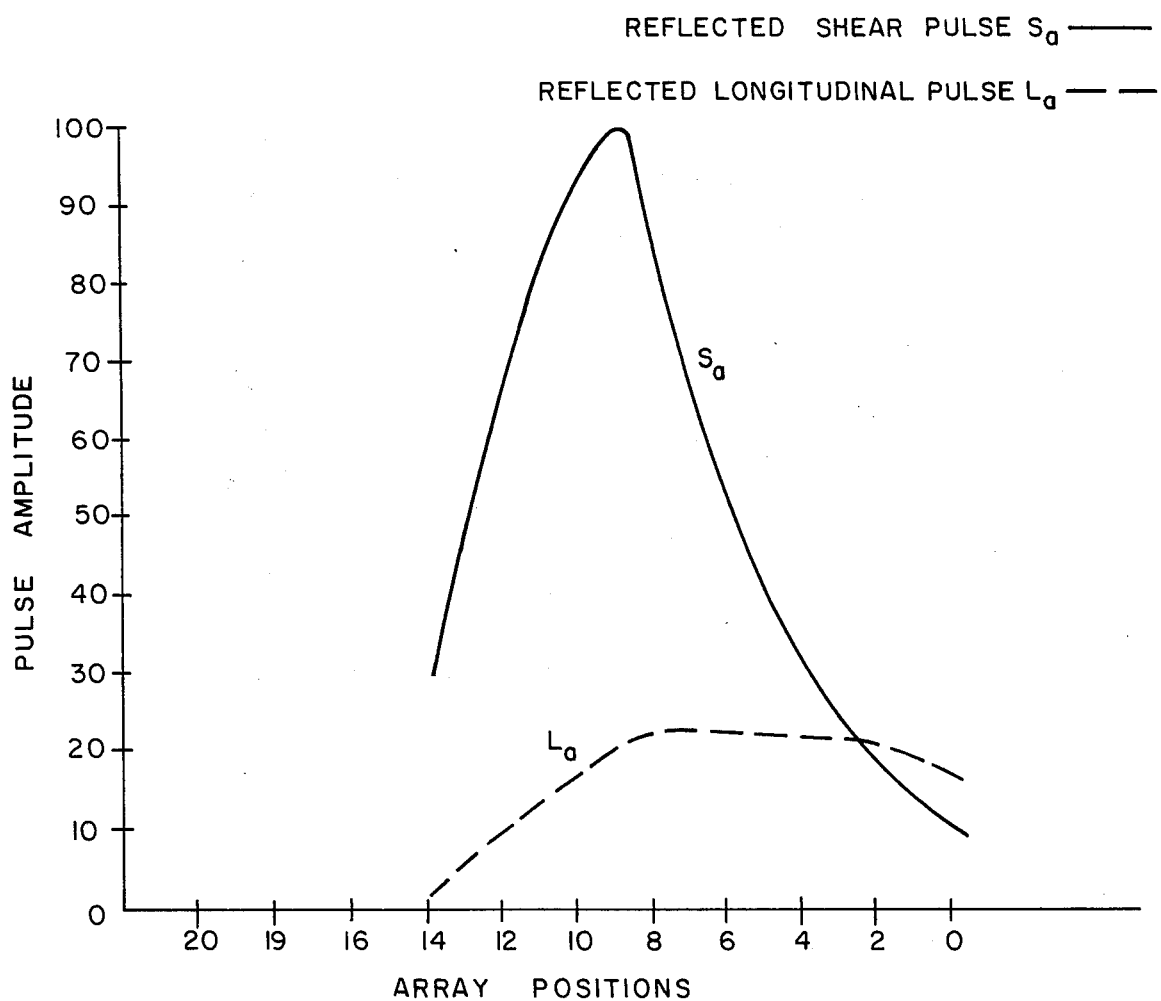

FIG. 9 shows the relative amplitudes of probe A's reflected shear pulse ($S_a$) and the associated reflected longitudinal pulse ($L_a$) returned by a crack-like defect upon a far surface being insonified by moving probe A as shown in FIG. 8. The array positions along the graph's horizontal axis correspond to the array positions shown in FIG. 8. The amplitude of the $S_a$ pulse is designed to be larger than that of the $L_a$ pulse because the shear pulse suffers a greater loss than the longitudinal pulse in propagating through a coarse-grained or bimetallic material.

FIG. 10 shows the waveforms received when using only probe A in Mode II of the Multiple-Beam Technique at various array positions as shown in FIGS. 8 and 9.

(a) shows a waveform received from a crack in an uncladded specimen when probe A is used and the described array is positioned at array position 9 as shown in FIGS. 8 and 9. At this position, the $S_a$ pulse is maximum.

(b) shows a waveform received from a crack in a cladded test specimen when probe A is used and the described array is positioned at array position 9 as shown in FIGS. 8 and 9. At this position, the $S_a$ pulse is maximum.

(c) shows a waveform received from a crack in an uncladded specimen when probe A is used and the described array is positioned at array position 3 as shown in FIGS. 8 and 9. At this position, the $L_a$ pulse is maximum.

(d) shows a waveform received from a crack in a cladded specimen when probe A is used and the described array is positioned at array position 3 as shown in FIGS. 8 and 9. At this position, the $L_a$ pulse is maximum.

(e) shows a waveform received from a crack in an uncladded specimen when probe A is used and the described array is positioned at array position 6 as shown in FIGS. 8 and 9. At this position, both the $S_a$ and $L_a$ pulses are substantial and neither is maximum.

Figure 10A:
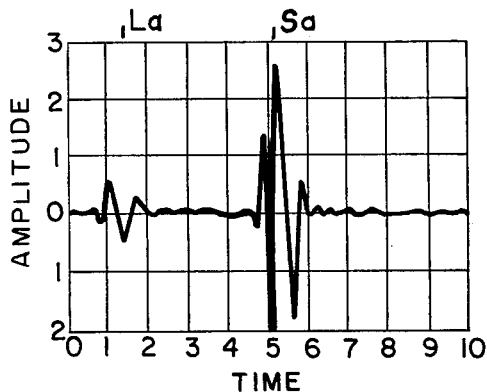
Figure 10B:
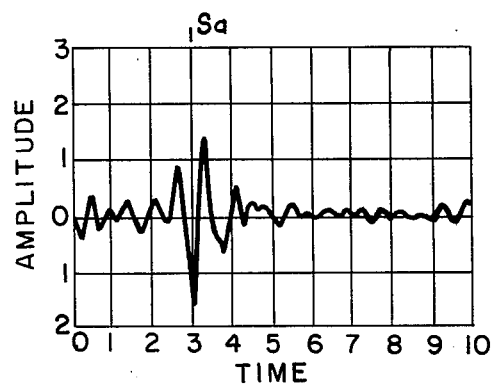
Figure 10C:
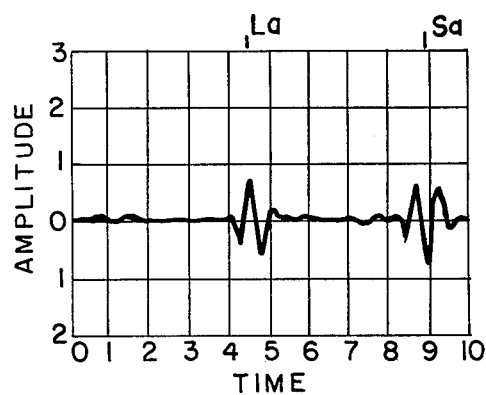
Figure 10D:
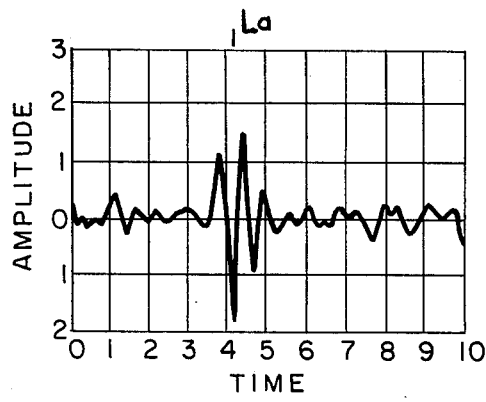

Comparison of the waveform of the uncladded test specimens shown in FIGS. 10(a), (c) and (e) show that the difference in time-of-arrival of the $S_a$ and $L_a$ pulses is practically independent of array position.

Figure 10E:
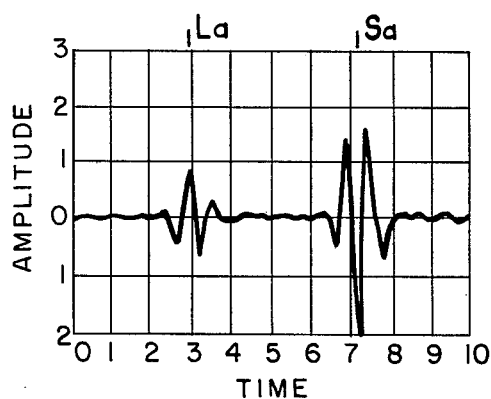

(f) shows a waveform received from a crack in a cladded test specimen when probe A is used and the described array is positioned at array position 6 as shown in FIGS. 8 and 9. At this position, both the $S_a$ pulse and the $L_a$ pulse have been compromised to capture substantial $S_a$ and $L_a$ pulses in a single waveform. Comparison of the waveform received from the cladded test specimen of FIG. 10(f) with that received from the uncladded test specimen of FIG. 10(e) shows that the difference in time-of-arrival of the $S_a$ and $L_a$ pulses is practically independent of test specimen composition. Mode II uses this associated pulse pattern as part of the call-confirmation process.

BACKGROUND OF THE INVENTION

1.1 Generally

Ultrasonics often provides the only practical method for the nondestructive evaluation (NDE) of austenitic pipes. Standard ultrasonic techniques usually yield reliable examination results. However, stainless steel cladding of the inside surface of the pipe adjacent to the weld, cladded to reduce the susceptibility of the wrought structure to intergranular stress corrosion cracking, has led to unexpected inspection difficulties. These difficulties have been linked to the anisotropy and inhomogeneity (acoustic impedance discontinuities) of bimetallic coarse-grained materials. Ref. 1. G. J. Gruber and H. Kapitza, "Reliability Evaluation of Six Ultrasonic Techniques for Cladded Pipe Examinations," in *Proceedings of 11th Nuclear Power Educational Seminar,* Southwest Research Institute, San Antonio, Tex., Apr. 20-23, 1981. Ref. 2. Proceedings of the *Committee on the Safety of Nuclear Installations Specialist Meeting on Reliability of Ultrasonic Inspection of Austenitic Materials and Components.* Ref. 3. Proceedings of the Workshop on *Ultrasonic Testing of Austenitic and Other Coarse-Grained Materials and Components,* Bundesanstalt fuer Materialpruefung, West Berlin, Sept. 25-26, 1980 (in German). Ref. 4. G. J. Gruber and H. Kapitza, "Detection of Surface Cracks in Bimetallic Coarse-Grained Structures—A Reliability Evaluation of Six Ultrasonic Techniques," Final Report on work performed as part of a scientific exchange program between Southwest Research Institute, San Antonio, Tex., and the Fraunhofer Institute for Nondestructive Testing, Saarbruecken, West Germany, 1980. The need for special ultrasonic techniques for the examination of the welds and heat-affected zones of cladded structures has been a strong incentive to research and development in this field. As a result, about a dozen novel ultrasonic techniques were developed in the past decade to improve the analysis and interpretation of test results. The Multiple-Beam Technique (MBT) was developed especially for cladded pipe applications. The results of an ultrasonic technique-reliability-evaluation study involving the MBT along with five other techniques are given in Refs. 1 and 4.

1.2 Inspection Difficulties

The problems associated with the ultrasonic testing of dissimilar metal welds (and clads) are well known. The Prior Art Disclosure Document submitted herewith contains numerous publications showing the state of the prior art. The main problem in the interpretation of test results is not due to high attenuation or lack of indications or sensitivity (gain), but to the many spurious (false, unwanted) indications (background interference—"interference"), that mask the weak defect (correct, 'wanted') indications ("signal"). Since spurious indications originating from harmless structural or geometrical anomalies occupy a region of the time domain in which defect indications could be present, the ultrasonic examiner is often unable to differentiate between the relevant and irrelevant parts of the received waveform. [Waveform is defined as the sum of overlapping defect and geometrical or structural echoes or indications (signal plus interference).] Tight surface-connected fatigue or stress corrosion cracks with irregular surfaces and unfavorable orientations may produce indications (signal) with insufficient amplitude to be distinguished from the disturbing indications of structural or geometrical anomalies (interference), and so they escape detection. This condition leads to missing the potentially harmful defect (Type II error). Conversely, structural or geometrical indications may be misinterpreted as produced by cracks (false alarming, Type I error). For crack indications with less than 6 dB signal-to-interference ratio (SIR), interpreting the waveform (i.e., deciding the presence or absence of a crack in the interrogated region) is marginal, and completely unreliable for crack indications with SIR values less than 3 dB.

2. STATISTICAL MODEL OF WAVE PROPAGATION

It is generally recognized that the reliability of an ultrasonic defect-detection technique depends not only on the type, size, orientation, and other characteristics of the defects, but also on the consistency of the basic material properties (grain size and orientation, fusion line roughness, elastic constants, etc.) throughout the test specimen and the choice of the monitored waveform parameters (amplitude, time-of-flight, etc.). Variations in the local values of basic material properties that determine the degree of spatial variability of acoustical properties (attenuation, velocity, etc.) affecting the waveform parameters are, in turn, governed by unavoidable or uncontrolled variations in the specimen manufacturing processes. Factors influencing the reliability of the ultrasonic inspection of a component or part may then be grouped as follows:

(1) Basic material properties
(2) Defect characteristics
(3) Monitored test parameters Uncontrolled or unknown variations in the local values of the basic acoustical properties have predominant influence on the ultrasonic inspectability of bimetallic coarse-grained structures. Up to now, little consideration has been given to sound propagation in composite austenitic structures, and a comprehensive statistical wave-propagation model for these structures is nonexistent. Before viable combinations of special probes and waveform operations can be selected for sufficiently reliable ultrasonic inspection of bimetallic stainless steel structures, the main causes of the inspection difficulties must be better understood. The degree of difficulty of the ultrasonic inspection is directly related to the extent of inhomogeneity and anisotropy in the structures to be examined.

Signal-reducing and interference-producing mechanisms postulated to model the propagation of pulsed ultrasound in the inhomogenous ocean with rough upper and lower boundaries (Ref. 5. R. J. Urick, *Principles of Underwater Sound for Engineers,* Chapter 8, McGraw-Hill Book Company, New York, 1967; Ref. 6. V.V. Ol'shevskii, *Characteristics of Sea Reverberation,* Consultants Bureau Translation from the Russian, New York, 1967.) and in anisotropic solids (Ref. 7. R. J. Hudgell and H. Seed, "Ultrasonic Longitudinal-Wave Examination of Austenitic Welds," *British Journal of NDT,* 22, 78–85, March 1980; Ref. 8. D. S. Kupperman and K. J. Reimann, "Effects of Microstructure of Ultrasonic Examination of Stainless Steel," in *Proceedings of the CSNI Specialist Meeting on the Ultrasonic Inspection of Reactor Components,* Risley, England, Sept. 27–29, 1976; Ref. 9. D. S. Kupperman and K. J. Reimann, "Effect of Shear-Wave Polarization on Defect Detection in Stainless Steel Weld Metal," *Ultrasonics,* 16, 21–27, January 1978); Ref. 10. P. Caussin, J. Cermak, and D. Verspeelt, "Factors Affecting the Reliability of the Ultrasonic Examination of Austenitic Compoents," in *Proceedings* of Ref. 2.) may be employed to guide efforts to develop improved ultrasonic techniques for bimetallic structures. Ultrasonic phenomena, that may explain the main sources of error in the pulse-echo examination of the welds and heat-affected zones of cladded stainless steel structures, are collected in Tables 1 and 2 together with their causes and effects. A phenomenon may have multiple effects, and the same effect may be the result of several phenomena. The SIR may be low in a given testing situation due to decreased signal or increased interference or both. The signal-reducing effects listed in Table 1 may lead to missing a particular defect, and the interference-producing effects listed in Table 2 may lead to false alarming. The adverse effects of the six signal-reducing phenomena (Mechanisms 1 through 6; see Table 1) and the six interference-producing phenomena (Mechanisms 7 through 12; see Table 2) are discussed under two headings: sources of Type II error and sources of Type I error. The reliability of an ultrasonic test appears to be refraction (mechanisms 1, 2, 9, and 10), reflection (Mechanism 3), and reverberation (Mechanisms 7 and 8) limited rather than attenuation (Mechanisms 4, 5, and 6) or noise (Mechanisms 11 and 12) limited. Reliability of a test is defined in Eq.(4) in terms of its Type I and Type II errors (see also FIG. 2).

TABLE 1

| SIGNAL-REDUCING MECHANISMS LEADING TO TYPE II ERROR (MISSING THE DEFECT) | | |
|---|---|---|
| Phenomenon | Cause(s) | Effect(s) |
| (1) Grain refraction | Velocity Gradient Grain Orientation | Beam Skewing Defocusing |
| (2) Fusionline Refraction | Velocity Discontinuity | Defocusing |
| (3) Fusionline Reflection | Impedance Discontinuity | Mode Conversion |
| (4) Surface Scattering | Interface Roughness | |
| (5) Volume Scattering | Grain Size | Attenuation |
| (6) Absorption | Heat Conductivity | |

TABLE 2

| INTERFERENCE-PRODUCING MECHANISMS LEADING TO TYPE I ERROR (FALSE ALARMING) | | |
|---|---|---|
| Phenomenon | Cause(s) | Effect(s) |
| (7) Surface Reverberation | Interface Roughness | Pulse Spreading |

TABLE 2-continued

INTERFERENCE-PRODUCING MECHANISMS
LEADING TO TYPE I ERROR (FALSE ALARMING)

| | Phenomenon | Cause(s) | Effect(s) |
|---|---|---|---|
| (8) | Volume Reverberation | Grain Size | |
| (9) | Grain Refraction | Grain Orientation Velocity Gradient | Focusing |
| (10) | Fusionline Refraction | Velocity Discontinuity | |
| (11) | Material Noise | Acoustic Emission | Amplitude Fluctuations |
| (12) | Electronic Noise | Thermal Agitation | |

2.1 Sources of Type II Error

In propagating from one point to another in a bimetallic coarse-grained structure, portions of the ultrasonic energy are directed away (refracted, reflected, or scattered) or converted into heat (absorbed) and lost as far as a particular receiver is concerned. The wave phenomena leading to beam curvature ("skewing"), beam widening ("defocusing"), mode conversion, and attenuation are discussed below.

2.1.1 Beam Skewing

During welding (and cladding), the grains grow parallel to their <100> crystallographic axis and along the heat dissipation lines. The columnar grains are unidirectional (nearly vertical) only in the vicinity of the center of the weld. (Refs. 7 and 10) The grains can grow epitaxially from one weld (or clad) run to another and are about 1 mm wide and up to several centimeters long. (Ref. 11. J. P. Launay, J. J. Olivera, and B. Trumpff, "Contribution to Improving Ultrasonic Testing of Thick Bimetallic Welds," in *Proceedings* of Reference 2.) Significant variations in the dendritic structure occur between the runs in the planes perpendicular to the weld (or clad) axis. Austenitic weldments and cladding are then anisotropic, at least in the planes perpendicular to the weld (or clad) axis. (Ref. 7)

The dependence of sound velocity on the direction of wave propagation in austenitic weldments and claddings is a result of two observations: (1) ultrasonic waves propagate along preferred paths relative to the axis of the columnar grains, and (2) the orientation of the grains varies along a given metal path. Under the condition of optimum beam-to-grain-orientation angle ($\phi=45$ degrees), the beam propagates along its expected direction, the signal amplitude is maximum (minimum propagation loss), and the transit time is minimum (maximum wave velocity). In propagating through the adjacent regions of an anisotropic metal characterized by optimum and various suboptimum beam-to-grain-orientation angles ($\phi \leq 44$ degrees and $\phi \geq 46$ degrees), the beam continuously undergoes bending. Snell's law applies: the sound rays always bend toward regions of lower velocity. When propagating through polycrystalline austenitic clad or weld metals, the beam angle increases in regions characterized by $\phi \leq 44$ degrees, and it decreases in regions with $\phi \geq 46$ degrees. The net effect of the many elemental ray bendings taking place in the interior of an anisotropic metal is termed beam skewing. (Ref. 7)

The columnar grains in clad and weld metals are randomly oriented. For this reason, long and straight sound paths associated with low propagation losses ("preferred paths") cannot be formed in these metals. Random fluctuations in $\phi$ of only a few degrees on either side of the optimum 45-degree value can lead to extensive beam skewing and associated decreases in the probability of crack detection.

It is not possible to calculate the profile of an ultrasonic beam (beam angle and width) as it propagates through a coarse-grained metal with randomly oriented columnar grains. The microstructure of an anisotropic metal could entrap the beam and bend it in a completely different direction. Thus, a straight-beam probe could be transformed into an angle-beam probe (Ref. 7) or vice versa. Ref. 12. X. Edelmann, "The Practical Application of Ultrasonic Testing of Austenitic Weld Joints," *materials Evaluation*, 37, 47–51, September 1979. The skewing of the beam could be as high as 30 percent of its nominal value so that a 70-degree beam, for example, might not be transmitted at all. (Ref. 10)

2.1.2 Defocusing

The anisotropy of clad and weld metals affects not only the angle, but also the width of the ultrasonic beam received by a pulse-echo probe. (Ref. 7; Ref. 13. H. Kapitza and K. Goebbels, "Physical of Ultrasonic Scattering," in *Proceedings* of Ref. 3; Ref. 14. H. A. Stelling, "Improvement of the Inspectability of Coarse-Grained Components by Adaptation of the Technique of the Structure," in *Proceedings* of Ref. 3.) In some regions of the anisotropic metal, the beam can become wider, while in other regions it can become narrower than what it would be were the metal isotropic. Beam widening (defocusing) and narrowing (focusing) are the results of Snell's law. For each probe position, the outer and inner parts of the beam pass through different columnar structures. It is, therefore, conceivable that, compared to the inner rays, the outer rays refract differently. Also, compared to the right part of the beam, its left part refracts differently.

The variations in beamwidth along a given curved metal path can be likened to the formation of "hot" spots (convergence zones) and "cold" spots (divergence zones) in the SOFAR-channel of the ocean. (In underwater acoustics, the acronym SOFAR is for SOund Fixing and Ranging.) (Ref. 5) The SOFAR-channel is a consequence of the characteristic sound velocity profile of the deep sea. The minimum in the sound velocity profile causes the sea to behave like a lens; on either side of the velocity minimum, the velocity gradient continually bends the sound rays toward the depth of mininum velocity. Hot spots are the result of convergent rays, and divergent rays result in cold spots.

Along the skewed sound path in an anisotropic metal, the hot spots are most likely to be found in regions where the beam-to-grain-orientation angle is in the neighborhood of 45 degrees. Cold spots, on the other hand, are most likely to be found in regions where the beam encounters the columnar grains at angles less than 15 degrees or more than 75 degrees. Together with beam skewing, defocusing accounts for the major part of the propagation loss in monometallic coarse-grained structures.

Ganglbauer, et al. have shown that fusion-line refraction resulting from the velocity discontinuities at the material interfaces of bimetallic coarse-grained structures can also lead to the formation of hot and cold spots in welded and/or cladded structures. (Ref. 15. O. Ganglbauer, F. Wallner, and R. Frielinghaus, "Contributions to the Ultrasonic Testing of Austenitic Welds Using Longitudinal Angle-Beam Probes," in *Proceed-* ings of Ninth World Conference on Nondestructive Testing, Melbourne, 1979; Ref. 16. O. Ganglbauer, F. Wallner, and R. Frielinghaus, "Influence of the Sound Velocity on Test Results," In *Proceedings* of Ref. 3). The curved and irregular fusion lines are intercepted by the individual rays of the sound beam in the base material at different angles. Rather than remaining parallel, the refracted rays may converge or diverge in a particular region of the weld or clad metal. The irregular surfaces of cracks behave similarly to the irregular fusion lines.

2.1.3. Mode Conversion

Specularly reflected energy as a result of the acoustical impedance discontinuities at the base-clad and base-weld metal interfaces can be another reason for the small signal returned from a surface-connected crack. In the extreme case, a longitudinal wave may be converted into a shear wave (i.e., it suffers infinite propagation loss) or vice versa as a result of total internal reflection at the various interfaces. (Ref. 16)

2.1.4. Attenuation

Attenuation mechanisms include absorption and scattering. The classical thermal loss in heat-conducting metals in the ultrasonic mesurement range is quite small. (Ref. 17. W. P. Mason, *Physical Acoustics—Principles and Methods*, Volume I, Part A, page 76, Academic Press, New York and London, 1964). Therefore, heat conductivity as a cause of attenuation is outweighed by the other two attenuation mechanisms (i.e., interface and grain scattering).

The most notable inhomogeneities contained within the interior and on or near the fusion lines of bimetallic coarse-grained structures are, respectively, the acoustically large grains and rough interfaces. (A dimension is considered to be acoustically large when it is comparable to or greater than the wavelength.) Since these imhomogeneities represent discontinuities in the acoustical impedance, they intercept and reradiate (i.e., scatter), theoretically in all directions, a portion of the ultrasonic energy. The energy removed by the large grains and rough interfaces from the ultrasonic wave is lost as far as a particular receiving probe is concerned. The net effect is increased attenuation.

Because of its roughness, the base-clad and base-weld material interfaces are profound scatterers or ultrasound. The removal of energy from the ultrasonic wave by the innumerable two-dimensional inhomogeneities located at or near the fusion lines or rough crack surfaces is termed surface scattering. Surface scattering in bimetallic structures is analogous to clutter in radar and bottom scattering in sonar. The ocean floor is an effective scatterer of underwater sound and acts to redistribute the energy incident upon it. The scattering sedimentary layer of the ocean is analogous to the corrosion-resistant layer of cladded pipes. Attenuation due to surface scattering increases with interface roughness in underwater acoustics as well as in the ultrasonics of bimetallic structures. (Ref. 18. N. V. Vinogradov, Yu. B. Sviridov, and N. V. Khimochenko, "Scattering of Ultrasonic Waves at the Interfaces of a Bimetallic Structure Produced by Explosion Welding," *Soviet Journal of Nondestructive Testing*, 12, 647–651, 1976.)

Grain size is generally recognized as the main cause of attenuation in coarse-grained materials (Refs. 10 and 13). The removal of energy from the ultrasonic wave by the innumerable three-dimensional inhomogeneities (i.e., the grains) is termed volume scattering. In fine-grained materials, the wavelength of the ultrasound in the 1 to 10 MHz frequency range is much larger than the mean grain diameter. In this case, the intensity of the scattered wave is proportional to the volume of the anomalous region (i.e., to the third power of the mean grain diameter) and the fourth power of the frequency (Ref. 19. C.B. Officer, *Introduction to the Theory of Sound Transmission with Applications to the Ocean*, page 269, McGraw-Hill Book Co., New York, 1958.) (Rayleigh scattering). In coarse-grained materials, the wavelength is comparable to the mean grain diameter. Calculations for acoustically large volume scatterers are difficult; and, in addition to the size, the shape of the anomalous region becomes important.

2.2 Sources of Type I Error

In propagating from one point to another in a bimetallic coarse-grained structure, indications above the recording level may be produced by backscattering from and unintentional focusing-in on the many harmless structural and geometrical anomalies. Random noise in the material or the electronics is much less likely to be a source of false alarming. The causes and effects of the six postulated interference-producing phenomena listed in Table 2 are discussed below.

2.2.1 Pulse Spreading

The sum of backscattering contributions from all inhomogeneities distributed along or near the rough material interfaces or crack surfaces of a bimetallic structure is termed surface reverberation (Ref. 5). The most disturbing aspect of the ultrasonic inspection of bimetallic structures is the highly reverberant nature of the clad and weld layers. The innumerable scattering centers of the rough base-clade and base-weld interfaces and crack surfaces may intercept, redistribute, and return a significant part of the ultrasonic energy in the direction of the pulse-echo probe. The ultrasonic pulse entering the clade (or weld) layer from the base material will suffer multiple reflections between its upper and lower (or right and left) boundaries and emerge at the pulse-echo probe as another series of reverberation echoes. The superposition of several decaying series of surface- and layer-reverberation echoes may produce an interference wave field of large amplitude so as to obscure the signal wave field associated with the presence of a surface-connected crack in the interrogated region. The radio-frequency (RF) envelope contains many irregular blobs of approximately the same duration as that of the transmitted pulse (Ref. 5). This effect is termed pulse spreading.

Because the surface reverberation echoes in a bimetallic structure are received along different metal paths, the amplitudes and arrival times of the blobs within the reverberation envelope may change significantly with slight movement of the pulse-echo probe. The reverberation envelope may also change drastically with slight shift in the center frequency of the transmitted pulse. The coherence length of surface reverberation decreases with increasing frequency (Ref. 5).

On the basis of a simple geometrical model of two-dimensional scatterers, Urick (Ref. 5) has shown that the average level of background interference due to surface reverberation is directly proportional to the area of the statistically rough surface returning ultrasonic energy toward the pulse-echo probe at any one instant of time. Therefore, the wider the beam and the longer the transmitted pulse, the greater the interference due to surface reverberation.

The acoustically large grains located in the interior of a coarse-grained material may also intercept, redistribute, and return a significant part of the ultrasonic energy in the direction of the pulse-echo probe. The sum of backscattering contributions from all three-dimensional inhomogeneities of a coarse-grained structure is termed volume reverberation. Pulse spreading due to volume reverberation may be explained as follows. Consider a short ultrasonic pulse incident upon the scatterers in a small volume of coarse-grained material embedded in an otherwise homogeneous fine-grained material. The backscattering of the leading edge of the pulse by the far scatterers in the anomalous region may then arrive at the pulse-echo probe at the same time as the backscattering of the trailing end of the pulse by the near scatterers. However, the backscattering of the leading edge of the pulse by the near scatterers may arrive significantly earlier than the backscattering of the trailing end of the pulse by the far scatterers. The net effect is a blobby, prolonged reverberation envelope (Refs. 13 and Ref. 20. K. Beuter, R. von Klot, and A. Sahm, "Improved Detection of Defects in Highly Scattering Structures through Spatial and Spectral Averaging," In *Proceedings of Reference 3.*)

On the basis of a simple geometrical model of three-dimensional scatterers, Urick (Ref. 5) has shown that the average level of background intereference due to volume reverberation is directly proportional to the volume of inhomogeneities returning ultrasonic energy toward the pulse-echo probe at any one instant of time. Therefore, the wider of the beam and the longer the pulse, the greater the interference due to volume reverberation.

At some instance in time, reverberation echoes may be received simultaneously from the surface and volume scatterers of bimetallic coarse-grained structures. The contribution of each kind of reverberation must be estimated separately and combined to yield the level of interference at a given time. It is necessary to draw a ray diagram to visualize the locations of the reverberating surfaces and volumes to be encountered at different times after the transmission of an ultrasonic pulse.

2.2.2 Focusing

It is shown in Section 2.1.2 that the ultrasonic beam can not only widen (defocus) but also narrow (focus) as it propagates through anisotropic weld and clad metals. Accidental focusing-in on a harmless structural or geometrical anomaly can then be the result of not only the velocity gradients in the interior of weld and clad metals (Ref. 7), but also the velocity discontinuities at the irregular weld-base and clad-base interfaces (Ref. 13). Structural or geometrical anomalies located in the convergence zones of the skewed ultrasonic beam reflect more than their expected amount. Just as propagation losses due to defocusing (cold-spot formaion) may lead to missing a potentially harmful defect, propagation gains due to focusing (hot-spot formation) may lead to false alarming by a harmless anomaly.

2.2.3 Amplitude Fluctuations

The adverse effects hitherto discussed are due to the anisotropic, inhomogeneous, and heat-conducting nature of bimetallic coarse-grained structures. The signal and interference levels (and their ratio, SIR) have been found to vary randomly from point to point in the material, but not as a function of time for a given position of the pulse-echo probe. Time-variant amplitude fluctuations due to acoustic emissions in the material and electronic noise are usually negligible in the 1 to 10 MHz measurement range, but are included in Table 2 for the sake of completeness.

DETAILED DESCRIPTION OF THE PREFERRED EMBODIMENT

3. Statistical Model of Crack Detection

The process of extracting a signal from the background interference in which it is embedded is considered to be a form of hypothesis testing by statistical defect-detection theory. Two mutually exclusive hypotheses are set up regarding the presence of a defect in the interrogated region of the material: $H_o$, no defect is present, and $H_1$, a defect is present. A Type I error occurs when the examiner decides that a signal is present in the received waveform when, in fact, there is no defect in the ultrasonic beam. A Type II error occurs when the examiner decides there is no signal in the received waveform when, in fact, there is a defect in the interrogated region.

3.1 Threshold Setting

The indication-reporting process requires the setting of the threshold level or recording amplitude ($A_r$) such that when it is exceeded, the decision "crack present" will be made. The setting of the threshold level is, therefore, critical for the Type I and Type II errors. Since the crack-detection process is reverberation limited and the reverberation waveform varies randomly with probe position, it is difficult to judge the suitability of a threshold setting for a set of bimetallic coarse-grained specimens in advance. The defect echoes (signals) obtained with a typical specimen ("reference block") cannot be used to establish a single recording level for all the test specimens.

Figure 1:
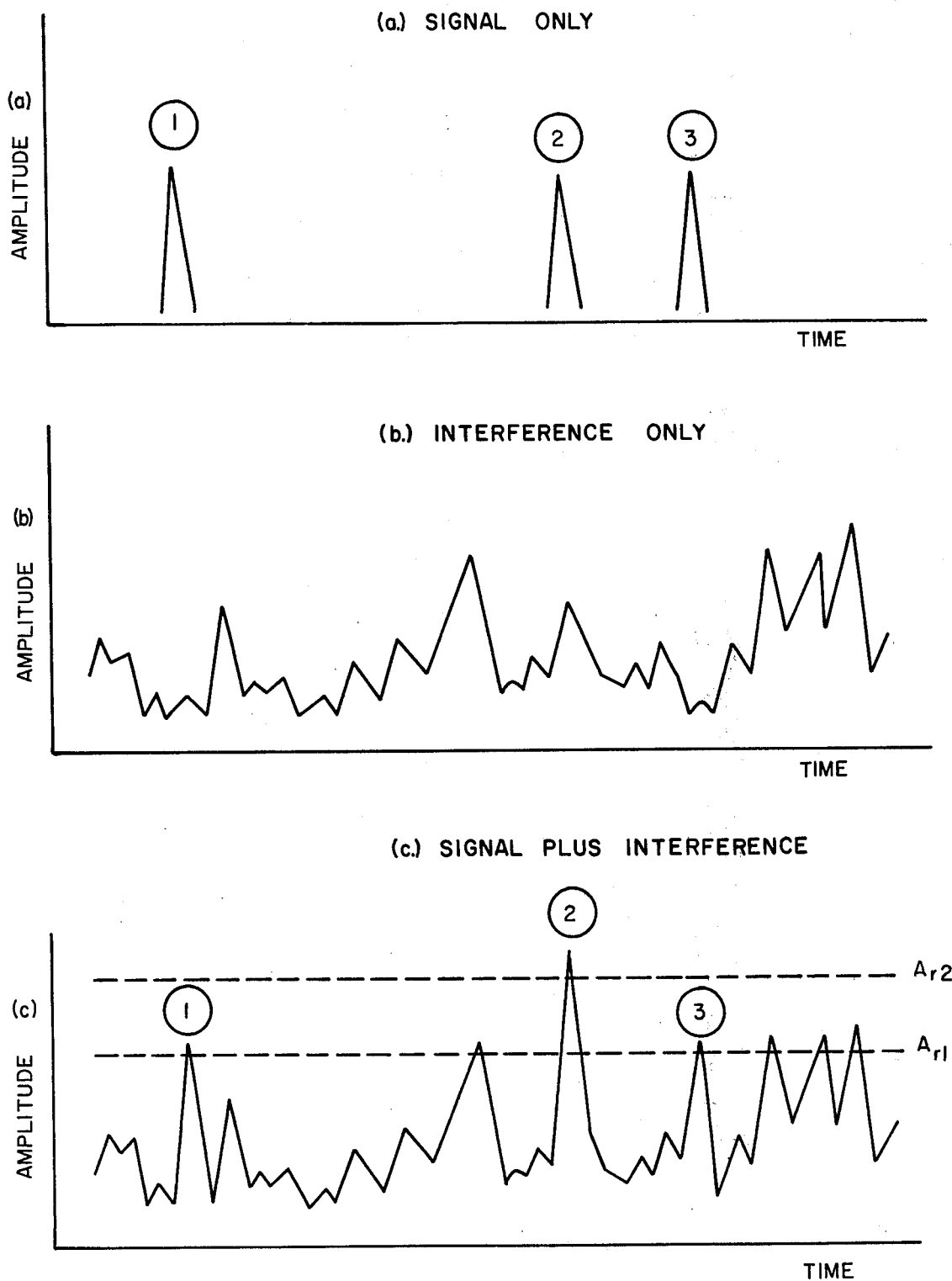
FIG. 1 illustrates the threshold setting dilemma of an ultrasonic tester.

The threshold setting dilemma is illustrated in FIG. 1. The three signals having the envelopes shown in FIG. 1(a), when added to the reverberation waveform of FIG. 1(b), appear as the signal-plus-interference waveform in FIG. 1(c). The ultrasonic examiner establishes a recording amplitude and categorically treats all indications with amplitudes above it ($A > A_r$) as signal and everything below it ($A < A_r$) as "no signal" (interference). If the threshold is set too low [see recording level $A_{r1}$ in FIG. 1(c)], undue false alarming will occur; if set too high [see recording level $A_{r2}$ in FIG. 1(c)], undue missing of the defect will occur. At the lower threshold, all three cracks are detected, but a number of false alarms will occur as well. At the higher threshold, only the second crack is detected, and there is no false alarming.

3.2 Reliability of Crack Detection

The interference model assumed in this analysis consists of a large number of statistically independent volume and surface reverberation sources (backscattering centers) located at various distances and oriented at various angles relative to the pulse-echo probe. The peak amplitudes of the reverberation echoes shown in FIG. 1(b) may follow the Gaussian distribution curve $P_o(A)$ shown on the left of FIG. 2. Reverberation is considered to be a Gaussian process since the number of backscatterers contributing to the process at a given time is generally large. The presence of a defect in the ultrasonic beam adds a constant to this probability density function and thus forms a second distribution curve. The probability density function $p_1(A)$ for the case of signal plus intereference is shown on the right of FIG. 2. The lower the threshold (i.e., the further $A_r$ is to the left in FIG. 2), the more defects will be detected; but, at the same time, more structural or geometrical anomalies will be regarded as cracks (Type I error). In contrast, the higher the threshold, (i.e., the further $A_r$ is to the right in FIG. 2), the fewer structural or geometrical anomalies will be detected; but, at the same time, the more cracks will be regarded as structural or geometrical anomalies (Type II error).

Figure 2:
FIG. 2 shows the probability density functions for a signal embedded in Gaussion reverberation and definitions of error probabilities $e_1$ and $e_2$ and signal-to-interference ratio (SIR).
Figure 2:
Figure 2:
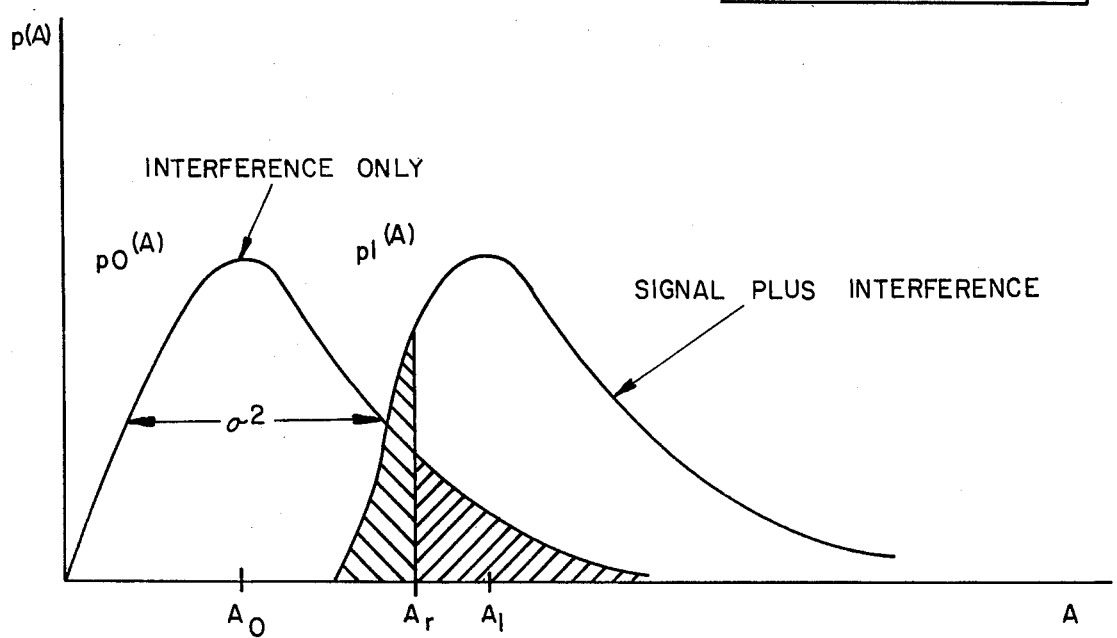

A few definitions are in order before leaving FIG. 2. The probability of false alarming ($e_1$) is given by the area under the "interference-only" curve to the right of $A_r$, and that of missing the defect ($e_2$) is given by the area under the "signal-plus-interference" curve to the left of $A_r$. The signal-to-interference ratio (SIR) is defined as the squared difference between the means $A_1$ and $A_o$ divided by the common variance of the two Gaussian probability density functions, $\sigma^2$. In symbols, $$SIR = \frac{(A_1 - A_o)^2}{\rho^2} \quad (1)$$

As the underclad or underweld cracks become deeper and the defect echoes become correspondingly larger, the two distribution curves in FIG. 2 broaden and their means separate, and thus a better resolution of the two hypotheses $H_o$ and $H_1$ results.

Ideally, all reported indications are correct ($e_1=0$), and all defects are detected ($e_2=0$). This is never the case for hard-to-inspect materials. Three performance indices can be defined:

(1) Defect detection probability $$D = (1 - e_2) \, 100\% \quad (2)$$

(2) Correct rejection probability $$C = (1 - e_1) \, 100\% \quad (3)$$

(3) Technique reliability $$R = 1 - \left(\frac{k_1 e_1 + k_2 e_2}{k_1 + k_2}\right) 100\% \quad (4)$$

where $k_1$ and $k_2$ are the costs associated with the two types of error. If the two error types are weighted equally, (i.e., if $k_1 = k_2 = 1$), then Equation (4) becomes $$R = \tfrac{1}{2}(D + C) \quad (5)$$

Mathematically, R is a measure of the total number of correct decisions.

Of the three performance indices, only R is sensitive to the adverse economic effects of both missing a crack at an early stage of its growth during a regular inservice inspection and stopping operations just to find out that a crack was not where it was supposed to be.

4. Multiple-Beam Technique

Some solutions to the low-SIR problems can be found in transmitted pulse design (pulseshaping) or beamforming while others can be found in waveform processing or pattern recognition. The SIR may be enhanced by a number of operations performed in the space, time, or frequency domains. The coherent (time-invariant) nature of the reverberation waveform dictated that operations performed in the space and frequency domains be considered as prime candidates for SIR enhancement. The special features and processes of the Multiple-Beam Technique (MBT) [the technique was named after its most characteristic feature (see Table 3)] are listed in Table 3 according to their suggested order of implementation. In compiling this list, special consideration was given to assure compatibility of these features and processes with each other. The Multiple-Beam Angle (MBA) device in its usual automated mode of operation (Mode I—Inspection) attempts to counteract the adverse effects of reverberation, beam skewing, and defocusing on the reliability of inspection by performing five special operations. The two main preventive measures of volume and surface reverberation (pulseshaping and beamforming) are introduced prior to pulse transmission (Feature 1—Short Pulses and Feature 2—Multiple Beams). Following waveform reception, three operations are performed (one in each of the frequency, time, and space domains). These are: Process 3—Spectral Averaging, Process 4—Directional Averaging, and Process 5—Spatial Filtering.

TABLE 3

SPECIAL FEATURES AND PROCESSES OF THE MULTIPLE-BEAM-ANGLE (MBA) DEVICE [MULTIPLE-BEAM-TECHNIQUE (MBT)]

| Operation | | Feature/Process | |
| --- | --- | --- | --- |
| Prior to Pulse Transmission | Pulseshaping and Beamforming | 1. 2. | Short Pulses Multiple Beams* |
| Following Waveform Reception | Waveform Processing | 1. | Multiple Bands*/ Spectral Averaging |
| | | 4. | Directional Averaging+ |
| | | 5. | Spatial Filtering+ |
| | Pattern Recognition | 6. | Multiple Pulses++ |

*Multiple Means Two or Three
+Used Only In The Automated Inspection Mode [Mode I - Inspection]
++Used Only In The Manual Reinspection Mode [Mode II - Confirmation]

To keep false alarming to acceptable levels, a pattern-recognition method, based on the observance of a pair of associated longitudinal- and shear-wave pulses (Feature 6—Multiple Pulses), is used in the device's manual reinspection mode (Mode II—Confirmation). A high-amplitude and, therefore, suspicious shear-wave indication or pulse (S) recorded in Mode I is considered to be unconfirmed and not reported until it is observed to be accompanied by its "satellite" longitudinal-wave indication or pulse (L) a known time ahead of it.

In general, a detection device is designed to operate in a rigid mode, and its parameters can not be changed readily. When one is able to vary the parameters of the detection process, one speaks of sequential detection. (Ref. 21. C. W. Horton, "Signal Processing of Underwater Acoustic Waves", United States Government Printing Office, Washington, D.C., 1969.)

The two-step process which uses the results of urine- and blood-sugar-level tests to estimate the prevalence of diabetes in a human population serves as an example of sequential detection. Only persons who test positive on the urine test are normally administered the blood test. The first test is more sensitive and the second test is more specific.

Two independent ultrasonic tests may be combined in series or in parallel (i.e., they may be performed in succession or simultaneously). When the tests are combined in parallel, the interrogated region of the test specimen is considered to contain a defect if it tests positive to any of the tests. The interrogated region is considered to be free of defects if it tests negative to all tests. A combination of tests in parallel enhances the sensitivity of the examination, but reduces its specificity. "Sensitivity" denotes defect detection probability, defined as $D=1-e_2$ where $e_2$ is the Type II error (missing the defect). "Specificity" denotes false-indication-rejection (correct rejection) probability, defined as $C=1-e_1$ where $e_1$ is the Type I error (false alarming).

When two tests are combined in series, the interrogated region of the test specimen is considered to contain a defect if it tests positive to each of the tests. The interrogated region is considered to be free of defects if it tests negative to any of the tests. A combination of tests in series enhances the specificity of the examination, but reduces its sensitivity.

Figure 3:
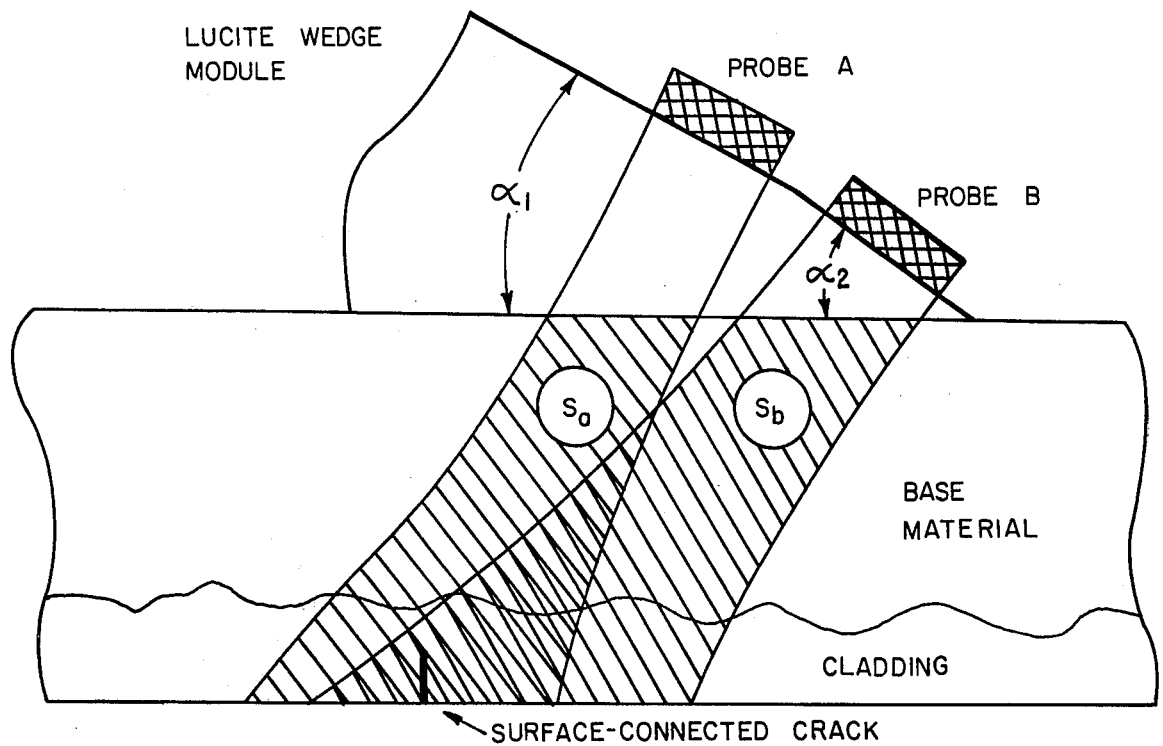
FIG. 3 shows the use of multiple beams in the inspection mode of operation (Mode I) of the Multiple-Beam-Angle device.

Two combinations of the three beams produced by the elements of the nonlinear MBA-device shown in FIGS. 3 and 7 offer several opportunities to increase the reliability of inspection. Even though the $L_a$, $S_a$, and $S_b$ beams overlap, the reverberation waveforms received by the two probes may be considered to be independent of one another and of the crack echoes. A parallel combination of tests, using the $S_a$ or $S_b$ beam shown in FIGS. 3 and 4, was designed to increase the defect detection probability (D). A series combination of tests, using the $S_a$ (or $S_b$) and $L_a$ beams shown in FIGS. 7 and 8, was designed to increase the probability of correct rejection (C).

The sequential operation of the MBA device is discussed in more detail below in terms of its unique probe design and other salient features and processes.

4.1 Mode I—Inspection By Amplitude Recording

The amplitude-dependent and recording-level-sensitive automated mode of operation of the MBA device uses both elements of the nonlinear array shown in FIG. 3. A lucite wedge module with two platforms, inclined to each other by a small angle (less than 10 degrees), is fitted with two highly damped pulse-echo probes. The platform inclination angle $\alpha_2$ for the probe in the back (Probe B) is larger than the critical angle for longitudinal waves in austenitic stainless steel materials (about 29 degrees), so that this probe transmits only a standard shear wave ($S_b$) into the specimen. For the purpose of introducing redundancy (and thereby a higher degree of reliability) into the crack-detection process, the platform inclination angle $\alpha_1$ for the probe ahead (Probe A) is chosen to be somewhat less than 29 degrees. This probe then transmits not only a shear wave ($S_a$), but also a longitudinal wave ($L_a$) into the specimen. The longitudinal wave transmitted into the specimen by Probe A is not shown in FIG. 3 because it is used only in the device's second mode of operation. The diverging S beams of FIGS. 3 and 4 are inclined to each other by about 10 degrees and overlap in the cladding region, which may or may not contain a surface-connected crack.

To facilitate real-time waveform processing (Process 4—Directional Averaging and Process 5—Spatial Filtering), consideration must be given to the minimization of the difference in the arrival times of the crack echoes received in the two channels (A and B) of the transmit-receive ultrasonic instrument. In other words, the coincidence of the energies partitioned into two parts (channels) is desired not only in the space domain (overlapping incident beams), but also in the time domain (overlapping received pulses). While the lucite path for the $S_a$ pulse is longer than that for the $S_b$ pulse, the reverse is the case for the metal paths. It is, therefore, possible to make the total time-equivalent path (in effect, the time of flight) from the probe to the surface crack and back statistically speaking the same for the two pulses. While being connected electrically in parallel, the two probes are to be moved up and down on their respective platforms relative to each other until the $S_a$ and $S_b$ pulses appear at the same position on the oscilloscope screen. The pulses $S_a$, $S_b$, and $S_{ab}=S_{ba}$ ("crosstalk") returning from the base of the surface crack in the two channels then reinforce each other with little, if any, buildup of the reverberation echoes from the clad interface and layer. The net effect is an improvement in the SIR.

In general, the SIR may be enhanced by partitioning the transmitted energy in the space, time, or frequency domains and performing averaging, filtering, and pattern-recognition operations on the received waveform in any of these domains. However, the coherent nature of the interference wave field in bimetallic coarse-grained structures rules out simple waveform averaging in the time domain as an effective statistical method for improving the SIR. To suppress the reverberation echoes to a greater degree than the defect echoes, the interference wave field must be decorrelated prior to waveform averaging.

The reverberation echoes can be made incoherent by varying the center frequency, beam angle, or probe position from one transmitted pulse to the next. Since defect echoes generally resist slight variations in these measurement parameters, opportunities exist for SIR improvement through frequency, beam-angle, or probe-position manipulation. (Ref. 22. S. Kraus, R. Neumann, and K. Goebbels, "Application of a Fast Signal Averaging Unit for the Ultrasonic Testing of Materials with High Coherent Noise Level," in *Proceedings of the Ninth World Conference on Nondestructive Testing*, Melbourne, 1979.)

A large number of statistically independent waveforms are usually needed to average out any high-amplitude reverberation echoes which, while occuring only occasionally, can lead to false alarming. The maximum number of decorrelated reverberation waveforms can be obtained with a periodic variation of the center frequency of the transmitted pulse (frequency wobbling). (Ref. 23. V. D. Koryachenko, "Statistical Processing of Flaw Detector Signals to Enhance the Signal-to-Noise Ratio Associated with Structural Reverberation Noise," *Soviet Journal of NDT*, 11, 69–75, February 1975.) Probe scanning results in significantly less reverberation decorrelation, and thus fewer statistically independent waveforms than frequency wobbling. The fewest number of statistically independent reverberation waveforms can be obtained with a variation of the duration of the transmitted pulse.

The use of short pulses in the MBT (Feature 1) permits a wide distribution (partitioning) of the transmitted energy in the frequency domain. Each independent frequency band contains additional information about the presence or absence of a crack in the interrogated region. The smoothing effect of frequency manipulation on the reverberation echoes can be exploited by transmitting short pulses, by filtering the received waveform into adjacent bands (Feature 3—Multiple Bands), and by averaging the filtered waveforms (Ref. 24. V. L. Newhouse, "Flaw-to-Grain Echo Enhancement by Frequency Agility," in *Proceedings* of Ref. 2.) (Process 3—Spectral Averaging).

The use of multiple beams in the MBT (Feature 2) permits a wide distribution (three-way partitioning) of the transmitted energy in the space domain. The smoothing effects of beam-angle manipulation and linear probe scanning on the reverberation echoes can be exploited by splitting the transmitted shear-wave energy into two overlapping beams ($S_a$ and $S_b$), by adding the waveforms received from neighboring interrogated volumes (Process 4—Directional Averaging), and by processing the linear scans with a low-pass filter (Process 5—Spatial Filtering). More on the three special waveform-processing operations of the MBT follows.

4.1.1 Spectral Averaging

The selection of frequency ranges ["optimum frequencies" and "optimum bandwidths"] (Ref. 25. H. A. Crostack and W. Oppermann, "Some Fundamental Aspects of Testing Austenitic Steel Structures by Ultrasound," in *Proceedings* of Ref. 2; Ref. 26. W. Opperman and H. A. Crostack, "Principles of the Controlled-Signal Technique," in *Proceedings* of Ref. 3.) for the reliable detection of surface cracks in bimetallic coarse-grained structures is a difficult task, involving the following considerations:

(1) Unlike the crack echoes, the reverberation echoes are strongly influenced by the ratio of the dominant wavelength to the mean interface roughness and grain size in the path of the ultrasound.

(2) While the reverberation level is less at the lower frequencies (<2 MHz), the transmitted energy may be distributed into a wide band more readily at the higher probe-resonance frequencies (<2 MHz).

(3) The shape as well as the amplitude of the reverberation spectrum varies significantly with probe position or beam angle.

(4) The optimum frequency for the detection of a crack, defined as the frequency at which the SIR is maximum, depends on its location.

The main conclusion to be drawn from these observations is that it is not possible to improve the detection of a crack or unknown location "by sharp frequency tuning of a narrowband ultrasonic system". (Ref. 27. E. Neumann, M. Roemer, R. Schenk, and K. Matthies, "On the Applicability of Ultrasonic Testing Techniques for Coarse-Grained Austenitic Welds," in *Proceedings* of Ref. 2.) For a test plate containing several underclad cracks, it may be more appropriate to select low frequencies to readily detect some of the cracks and then select high frequencies to detect some of the cracks missed with low frequencies. For some of the cracks, "the maintenance of optimum test frequency" (Ref. 25) could actually mean switching into another frequency band of the receiver. Multifrequency tests result in higher defect detection probability. (Ref. 28. H. A. Crostack, V. Deutsch, and M. Vogt, "Improvements in Ultrasonic Testing by Means of Narrow-Band Transmitter Pulses of Continuously Variable Frequency," *British Journal of NDT,* 22, 116-171, July 1980.)

A simple form of spectral averaging can be realized by filtering the waveform received at a fixed probe position from a fixed direction into two or three adjacent frequency bands and adding the filtered waveforms for an improvement of defect detectability (test sensitivity). The center frequencies of the first two receiver bands of the German Krautkraemer USIP 11 Ultrasonic Flaw Detector are at 1.1 and 4 MHz, and those of the first three bands of the American Sonic Mark IV Ultrasonic Flaw Detector are at 1, 2, and 5 MHz. Both of these widely used transmit-and-receive ultrasonic instruments are equipped with video (rectified) and RF-waveform display modes. The multiple receiver bands of these flaw detectors can be readily used for "split-spectrum processing" (Ref. 24) and spectral averaging of the waveforms received with a 2.25 MHz wideband probe.

4.1.2 Directional Averaging

In addition to selective spectral filtering, changing the region wherein backscattering will be produced by variation of the beam angle for a fixed probe position and frequency band provides another statistical method for improving the detectability of underclad cracks. (Ref. 22) The SIR enhancement achievable by beam-angle manipulation without probe movement in a given frequency band depends on the directivity pattern of the phase-locked MBA-device, the directivity pattern of the surface-connected crack, and the spatial characteristics of the reverberation wave field. The four reverberation waveforms received by the two halves of the stationary array ($W_{aa}$ and $W_{ba}$ in Channel A and $W_{bb}$ and $W_{ab}=W_{ab}$ in Channel B) are statistically independent time functions since the probe separation distance is greater than the coherence length of the interference wave field. It is very unlikely that the pulses transmitted separately by the two probes of the MBA-device into neighboring regions give rise to reverberation echoes in concert. The reverberation echoes can then be suppressed relative to the crack echoes by connecting the two pulse-echo probes in parallel. The simple addition of the four waveforms received in the two channels of the MBA-device is the essence of real-time directional averaging.

4.1.3 SPATIAL FILTERING

The peak amplitude of the bandpass-filtered and directionally averaged waveform in a carefully selected time window may be recorded to distinct advantage during the linear scans of the MBA-device in the direction perpendicular to the plane of the crack (x direction). As an underclad crack comes into the view of the MBA-device, there is a characteristic rise in the low-frequency content of the random amplitude function (peak amplitude versus x). The reason for the appearance of a low-frequency hump in the amplitude function in the vicinity of a crack is the multiple-beam feature of the device. The envelopes describing the rise and fall of the crack-reflected pulses $S_a$, $S_b$, and $S_{ab}=S_{ba}$ overlap to a randomly varying degree during a linear scan, and they generally peak out at different probe array positions so that the envelope contour resembles the "low-frequency" letter M. A low-pass spatial filter may, therefore, be gainfully used to improve the detectability of underclad (or underweld) cracks. The spectral-averaging, directional-averaging and spatial-filtering operations appear to be independent and the resulting SIR enhancements additive.

4.2 Mode II—Confirmation by Pattern Recognition

The high-amplitude shear-wave indications ($S_a$ or $S_b$) obtained with a parallel combination of tests (Mode I) are subject to reinspection (confirmation). The reliability of the crack-detection process may be further improved by combining the S-wave test with an L-wave test in series ($S_a$ or $S_b$ and $L_a$). The amplitude-independent manual mode of operation (Mode II) of the MBA-device also uses two incident beams, but now the two beams ($L_a$ and $S_a$) are produced by the same probe (see FIG. 7). Because the longitudinal wave travels nearly twice as fast as the shear wave in stainless steel materials, the crack echoes $L_a$ and $S_a$ arrive at probe A at different times. The simultaneous use of the two wave modes then permits a two-way partitioning of the transmitted energy not only in the space domain, but also in the time domain (Feature 6—Multiple Pulses). The thicker the test specimen, the larger the difference in time-of-arrival between the $L_a$ and $S_a$ pulses.

The most striking characteristic of the $L_a$ pulse is that it precedes the $S_a$ pulse by a time interval $\Delta$, that is practically independent of probe position. In contrast to the reverberation echoes that vary unpredictably and dramatically with probe movement ("easy come, easy go"), the crack echo pair resists changes in amplitude and $\Delta$ with slight probe movement. The LS echo pair appears to travel as if joined arm-in-arm to the left (or to the right) on the screen as the probe is moved toward (or away from) the surface crack. Pulses that remain a fixed time interval $\Delta$ apart during their travel on the screen are termed associated pulses. The larger of the echo pair is called the main pulse, and the smaller of the two is termed the satellite pulse. As shown in FIGS. 10(a), (c) and (e), the generally smaller (but faster, thus leading) L pulse may then be considered as the precursor satellite of the slower S pulse.

Satellite pulses form the basis of the amplitude-independent, pattern-recognition method developed for the characterization (as to shape and size) of an already detected defect. (Ref. 29. G. J. Gruber, "Ultrasonic Satellite-Pulse Technique for Characterizing Defects of Arbitrary Shape," patent pending in the U.S. Patent and Trademark Office, Ser. No. 142,216, filed on Apr. 21, 1980; Ref. 30. G. J. Gruber, "Satellite-Pulse Technique for the Characterization of Defects of Arbitrary Shape with Ultrasound," in *Abstract Proceedings of the 1980 Annual Meeting of the German Society of Nondestructive Testing*, Goettingen, May 12-14, 1980 (in German); Ref. 31. G. J. Gruber, "Defect Identification and Sizing by the Ultrasonic Satellite-Pulse Technique," *Journal of Nondestructive Evaluation*, May-June 1981). Planar (crack-like) defects give rise to precursor satellite pulses, and volumetric (void-like) defects yield postcursor satellite pulses.

In the confirmation mode of the MBT, the examiner is manually searching for an L pulse to accompany the high-amplitude S indication recorded during automatic scanning of the test specimen (Mode I). The S indication, suspected to have originated from a surface crack, is reported if, upon manual examination, the same region of the material tests positive also to the L-wave test. Starting from the position where the $S_a$ (or $S_b$) pulse is maximum, the probe must be moved away from the crack (to the right in FIG. 8) to maximize the amplitude of the L pulse. Aside from this characteristic echo dynamic behavior of the L pulse, the known constancy of the time interval during back and forth probe scanning can also be used to discriminate against "ghost satellites" (i.e., false L indications). The defect-confirmation process thus depends on the skill of the examiner to recognize the LS echo pair, provided that a defect is present in the interrogated region.

5. Apparatus and Method

The preferred embodiment and best mode of the invention involves use of an ultrasonic method to detect and confirm cracks in bimetallic or coarse-grained materials. It is to be understood, however, that many types of anomalies in many types of media can be reliably detected as is described and claimed herein. Further, the method is not limited to ultrasonic waves, but rather other mechanical or acoustical waves can be utilized where practicable.

The method of explanation herein is chosen to permit those skilled in the art of nondestructive testing to readily use the Multiple-Beam Technique. Because the waves transmitted and received in nondestructive testing are generally generated and observed as electronic signals, they are referred to in the industry as "pulses" or "signals". Further, echoes caused by the incident beams interacting with the defect are termed "signals" and all other echoes termed "interference".

The term "detection beams" as used herein describe aimed mechanical or acoustical waves which are of the same wave mode and which are used in the detection operation of the method. The detection beams used in the preferred embodiment are $S_a$ and $S_b$, although other waves or modes such as $L_a$ and $L_b$, etc. can be used. The term "confirmation beams" as used herein describe aimed mechanical or acoustical waves that have significant components of different wave modes. The confirmation beams used in the preferred embodiment have significant $S_a$ and $L_a$ wave components. The term "defect" is used herein to describe a test specimen anomaly of interest whether it be a desired anomaly or an undesired anomaly. Amplitude of a pulse is the electronic measure of the energy contained in that pulse. Difference in arrival times of the pulses are due to differences in the travel paths of the wave components. A transducer is used to convert short, electrical pulses into an incident beam of ultrasonic waves which is transmitted into the body being tested. Reliable detection and high resolution are attained by transmitting short pulses, resolving the returned signals with a resolution unit, and placing the probes at such distances and angles with regard to the suspected defect that the pulses received from the defect are of substantial amplitude above the background interference.

Pulse durations that may be used for inspecting steel pipes or plates range from 0.5 to 5.0 cycles. Preferable pulse durations range from 0.5 to 2 cycles for specimens less than 10 mm thick because longer pulses result in decreased pulse resolution and increased background interference. For thicker test specimens, longer pulse durations may be used depending upon the nature and extent of interference phenomena.

A short effective pulse is produced by combining a transmit-receive ultrasonic instrument with a short excitation pulse and a highly damped probe. Failure to effectively damp the probe or use long excitation pulses results in decreased resolution and increased interference.

The probe typically used is an unfocused probe because the Multiple-Beam Technique requires overlap between incident beams aimed in different directions. Focused probes with converging incident beams are of limited usefulness in usual applications of the technique.

Many center frequencies can be used. Ultrasonic operating frequencies from 1 to 10 MHz may be effectively used with the preferred probe-center-frequency range being from 1.5 to 3.0 MHz.

Received echoes are termed "substantial" when their amplitude exceeds twice the mean amplitude of the interference echoes. The receiving of substantial echoes is critically dependent upon the signal-to-interference ratio (SIR) as described above in connection with FIGS. 1 and 2.

A novel defect detection and confirmation device, termed the multiple-beam-angle device, was invented for use with the invented method. The multiple-beam-angle device (MBA) comprises at least one transmitting probe and at least one receiving probe (the transmitting and receiving probes may be the same or different transducers and may be located upon the same or different wedges), a resolution unit (usually a pulse-arrival-time device having a display, such as an oscilloscope), and at least one transmit-receive ultrasonic instrument. The combination of transmitter (pulser), receiver, and pulse-arrival-time-display device (oscilloscope), either within a single instrument or within separate instruments is termed an "ultrasonic test unit". The ultrasonic test unit preferably should be capable of high frequency transmission and reception, have a broad possible frequency range for both transmission and reception, and be capable of reasonably high resolution. An ultrasonic test unit which may be used is a Mark I ultrasonic Flaw Detector manufactured by Sonic Instruments, Inc. of Trenton, N.J. More than one probe each located upon separate platforms are preferably used and are collectively described as a probe array or an array. The preferred array described herein comprises two probes. This is for the purpose of simplicity only. More than two probes can be used.

As shown in FIGS. 3 and 7, the shoe or wedge is typically a generally triangular shaped object comprised of Lucite or some other material that does not greatly attenuate ultrasonic waves transmitted through it. A shoe absorber may be beneficially put upon the wedge to attenuate ultrasonic waves which are reflected off the surfaces of the shoe back into the wedge. The shoe absorber may be comprised of any damping material, but is typically polyurethane.

The symbol $\alpha$ is used herein to mean the various platform-to-test-specimen angles employed in a given use of the Multiple-Beam Technique. As shown in FIGS. 3 and 7, $\alpha_1$ identifying the angle between the platform of probe A and the test specimen is used herein to designate the platform-to-test-specimen angle for the platform upon which the probe used in the confirmation operation (Mode II) of the Multiple-Beam Technique is placed. The angle $\alpha_2$ identifying the angle between the platform of probe B and the test specimen is used to designate the platform-to-test-specimen angle for the platform upon which the probe used only in detection operation (Mode I) of the Multiple-Beam Technique is placed. As shown in FIGS. 3 and 7, $\alpha_1$ is associated with probe A and $\alpha_2$ is associated with probe B.

As shown in FIGS. 3 and 7, the wedge preferably used has two platforms upon which probe A and probe B are located. A wedge may be designed to have one or more platforms and one or more probes can be located upon any platform. The angles $\alpha_1$ and $\alpha_2$ as shown in FIGS. 3 and 7 for the probe A and probe B platforms are 27° and 35°, respectively. Practically any combination of angles can be chosen as long as one of the platforms has a small $\alpha$ angle so at least one of the probes transmits a significant longitudinal wave in addition to a shear wave normally used in ultrasonic testing and so these beams will overlap in the regions of interest in the test specimen. The desired overlap must occur both between the $S_a$ and $S_b$ beams as shown in FIG. 3, and for the $L_a$ and $S_a$ beams as shown in FIG. 7. The two primary angular array-design considerations therefore are (1) choosing an $\alpha_1$ angle for probe A which will yield an appropriate $S_a$ to $L_a$ peak signal amplitude ratio range in the regions of interest in the test specimen, (2) choosing a roof angle ($\alpha_2-\alpha_1$=roof angle) which will yield an apporpriate $S_a$ to $S_b$ peak signal amplitude ratio range in the regions of interest in the test specimen.

For test specimens comprised of steel and wedges comprised of lucite, the $\alpha_1$ angle for probe A may not be larger than 29°. This angle is designated as the "critical angle" because platforms with angles larger than 29° will not permit the probe located thereon to generate sufficient longitudinal waves within the test specimen. Any $\alpha_1$ angle between 0° and 29° may be used although $\alpha_1$ angles in the range of 22° to 27° are preferable.

The preferred $S_a$ to $L_a$ peak signal amplitude ratio range for a cladded or coarse-grained specimen is about 2:1 to about 3:1. The $S_a$ to $L_a$ signals having a peak amplitude ratio ranging from about 1:4 to about 4:1 could conceivably be used. To obtain an $S_a$ to $L_a$ peak signal amplitude ratio of about 1:1 in the cladded specimen, it is often necessary that the $\alpha_1$ angle be sufficiently low to yield a $S_a$ to $L_a$ peak signal amplitude ratio no greater than about 4:1 in an uncladded specimen. This is because the $S_a$ beam suffers greater propagation loss in a typical cladded specimen than does the $L_a$ beam.

The preferred $S_a$ to $S_b$ peak signal amplitude ratio range for a cladded or coarse-grained specimen is about 1:2 to about 2:1. The $S_a$ to $S_b$ signals having a peak amplitude ratio ranging from about 1:4 to about 4:1 could conceivably be used. The preferable roof angle varies inversely with the thickness of the test specimen. The thicker the test specimen, the smaller the preferred value of the roof angle. For examination of a region upon the far surface of a test specimen of 10 to 100 millimeters thick, acceptable roof angles may range from 6° to 12°. For thin test specimens, 8° is the preferable roof angle.

Practically any ultrasonic transducer may be used as a probe. The preferred embodiment uses NDT International Inc. Probe Nos. C-6 (2.25 MHz) or C-1 (5 MHz). The probes may be adjustably fixed upon the platforms of the wedge or wedges. In the preferred embodiment, probes A and B are located upon different platforms of the same wedge as shown in FIGS. 3 and 7.

Each probe is connected to a separate channel of an ultrasonic test unit. The ultrasonic test unit is used in the transmit-receive (pulse-echo) mode rather than the pitch catch mode. In the transmit-receive mode, each probe sends pulses and each probe receives echoes.

A couplant solution typically comprised of a light oil is applied to the bottom surface of the wedge prior to use to facilitate transmission of the ultrasonic energy from the lucite into the test specimen.

The Multiple-Beam Technique is comprised of three major parts: Calibration; Inspection (Mode I); and Confirmation (Mode II).

Three calibration steps must be taken prior to data collection; (1) calibration of the amplitude scale (vertical scale) of the oscilloscope, (2) phase locking of the received $S_a$ and $S_b$ signals, and (3) calibration of the time scale (horizontal scale) of the oscilloscope. The goal of calibration is to eliminate the difference in arrival time between the $S_a$ signal and the $S_b$ signal for the test specimen and to superimpose the received $S_a$ and $S_b$ signals to the extent possible. This is done by locating the $S_a$ signal upon an oscilloscope, locating the $S_b$ signal upon an oscilloscope, and adjusting the relative positions of the probes upon their respective platforms to superimpose the $S_a$ and $S_b$ signals. Difficulties in exactly superimposing the $S_a$ and $S_b$ signals are caused by the interference due to test specimen's cladding and its coarse-grained nature together with the different arrival times of $S_a$ and $S_b$ pulses at the wedge-specimen interface due to the deliberate placement of probe A and probe B at different angles and different distances with regard to the test specimen.

The first step in calibration is to phase lock the $S_a$ and $S_b$ signals received from a known reflector. This first involves locating the $S_a$ and $S_b$ signals. This is done for the $S_a$ signal by using probe A alone and judiciously moving it back and forth over the known ultrasonic reflector until the $S_a$ signal is observed and positively identified as the $S_a$ signal. The method of identifying an $S_a$ signal from a known reflector is known in the art and competent ultrasonic operators can perform this task. This $S_b$ signal from the known reflector is likewise observed and positively identified by using probe B alone.

After the $S_a$ and $S_b$ signals are identified, probes A and B are connected electrically in parallel to separate channels of the ultrasonic test unit and the $S_a$ and $S_b$ signals are superimposed to the extent possible. This is accomplished by adjusting the relative positions of the probes upon their respective platforms while observing the previously identified $S_a$ and $S_b$ signals that are now simultaneously shown on the oscilloscope. Although exact superimposition of the $S_a$ and $S_b$ signals is impossible, by judiciously moving the probes relative to each other, the degree of overlap between the $S_a$ and $S_b$ signals can be maximized.

As shown in FIG. 1, the second step in calibration is to select a threshold amplitude or recording level (gain setting) which will be useful in distinguishing substantial signals from the background interference. The calibration problem is referred to as the "threshold dilemma". The operator locates an ultrasonic reflector within the test specimen, such as a known corner, crack or notch, that can provide substantial echoes. The method of selecting appropriate recording amplitudes once a calibration reflector is located is described in detail above. There is no one recording amplitude ($A_r$) that is optimum for a set of given test specimens. Several recording amplitudes should be selected and used to obtain reliable results.

The third step in calibration is to calibrate the time scale of the oscilloscope. This involves locating the $S_a$ and $L_a$ signals from a known reflector and setting the time scale to simultaneously display both signals during significant probe movement. This is done by setting the time scale so that the time interval $\Delta$ between the $S_a$ and $L_a$ signals is in the range of 20% to 80% of the time window of the oscilloscope available for viewing and preferably 40% of the time window such as is shown in FIGS. 10(a), (c), (e), and (f). In some difficult-to-inspect specimens, the $S_a$ and $L_a$ signals will not be simultaneously observable and more sophisticated tracking means must be used, such as mathematically determining or recording the relationship of the confirmation $L_a$ and $S_a$ signals.

The Multiple-Beam-Angle device is now calibrated and ready to use in the inspection mode (Mode I).

Any defect in the interrogated zone of interest will reflect both the $S_a$ and $S_b$ transmitted pulses. Because of prior calibration, the $S_a$, and $S_{ab}$ ("cross talk") signals are added together in phase to produce a reinforced $S_a + S_b + S_{ab}$ sum signal. Because the overlapping interference echoes received by probe A and probe B are distributed randomly in phase and amplitude, it is unlikely upon statistical bases that the interference echoes will reinforce each other.

Figure 6A:
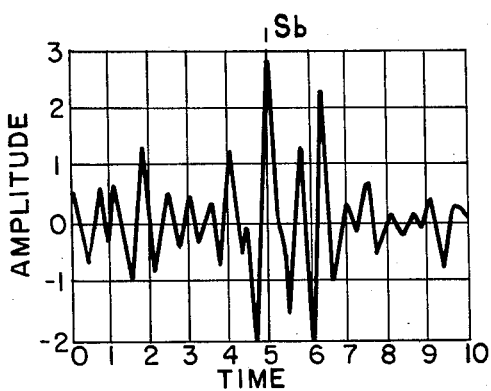
FIG. 6 shows the waveforms received when using an array of probe A and probe B in various combinations in Mode I of the Multiple-Beam Technique as shown in FIGS. 4 and 5 at a fixed array position.
Figure 6B:
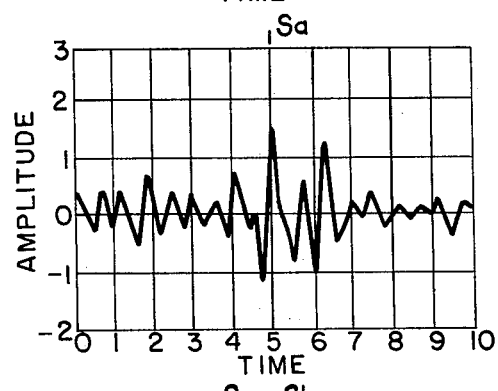
Figure 6C:
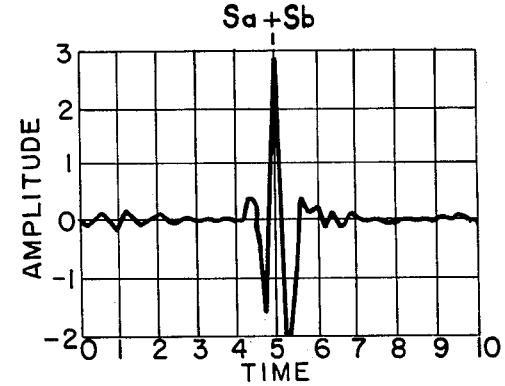
Figure 6D:
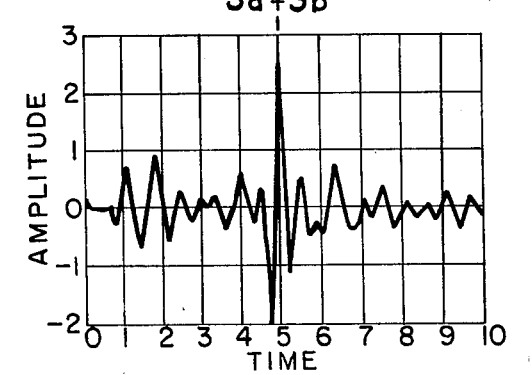

This process of canceling many unwanted reverberation echoes (interference) and reinforcing the wanted echoes (signals) due to the spatial separation between probe A and probe B by means of a summing device is called directional averaging. Mode I takes advantage of the sum signal being substantial as compared to the background interference ultrasonic echoes as is shown in FIG. 6(d).

Because of directional averaging, the interference level is greatly reduced relative to the signal level. Any echoes that are substantial compared to the background interferences are termed "called echoes" or "calls" and are presumed to indicate one or more defects (suspect defects).

The first step of Mode I is to position the array upon the test specimen so the $S_a$ and $S_b$ beams of the array will overlap in the region of interest in the test specimen. The $S_a$ and $S_b$ beams are transmitted into the test specimen by probes A and B, the echoes are received by the same or other probes and are resolved on the oscilloscope screen.

The array is slowly and steadily moved along the test specimen as is shown in FIG. 4 while insonifying the far surface of the test specimen as shown in FIG. 3.

FIG. 4 shows various numbered array positions upon the examination surface of an uncladded test specimen with regard to an ultrasonic wave reflector such as a crack-like defect upon the far surface of the specimen. The $S_a$ and $S_b$ incident shear-wave beams are shown emanating from the array at array position 10. The angles $\beta_1$ and $\beta_2$ represent the directions of the incident shear beams with respect to a line perpendicular to the examination surface. The resolution unit is set for video viewing of the rectified waveforms received. FIG. 5 shows the relative amplitudes of the $S_a$ and $S_b$ pulses reflected from a surface-connected crack insonified by the array as shown in FIG. 4. The array positions along the graph's horizontal axis correspond to the array positions shown in FIG. 4. The $S_b$ pulse is stronger than the $S_a$ pulse because, as shown in FIG. 3, the $\alpha_1$ angle is smaller for probe A than the $\beta_2$ angle for probe B. The peak amplitude of the $S_b$ pulse is larger than that of the $S_a$ pulse because probe A transits a longitudinal wave as well as a shear wave.

As an underclad crack comes into the view of the array, there is a characteristic rise in the low-frequency content of the random envelope function (peak amplitude versus array position) as shown in FIG. 5. The reason for the appearance of a low-frequency hump in the envelope function in the vicinity of a crack is the multiple-beam feature of the detector. The envelopes describing the rise and fall of the amplitudes of the crack-reflected pulses $S_a$, $S_b$, and $S_{ab} = S_{ba}$ overlap to a randomly varying degree during a linear scan, and they generally peak out at different array positions so that the envelope function resembles the "low-frequency" letter M as shown in FIG. 5. A low-pass spatial filter may, therefore, be gainfully used to improve the detectability of cracks.

FIG. 6 shows the waveforms received when using an array of probe A and probe B in various combinations in Mode I of the Multiple-Beam Technique as shown in FIGS. 4 and 5 at a fixed and compromised array position. FIG. 6(a) shows a waveform received from a crack in a cladded test specimen when only probe B is used and the described array is positioned at array position 15 as shown in FIGS. 4 and 5. FIG. 6(b) shows a waveform received from a crack in a cladded test specimen when only probe A is used and the described array is positioned at array position 15 as shown in FIGS. 4 and 5. FIG. 6(c) shows a waveform received from a crack in an uncladded test specimen when probes A and B are connected electrically in parallel and the described array is positioned at array position 15 as shown in FIGS. 4 and 5. FIG. 6(d) shows a waveform received from a crack in a cladded test specimen when both probe A and probe B are used in the described array and the array is positioned on the test specimen at array position 5 as shown in FIGS. 4 and 5.

Longitudinal waves can be used in Mode I rather than shear waves if the test specimen is very thick (in steel; in excess of 100 mm). The beams used in the detection operation (Mode I) are termed "detection beams" regardless of the type of beam used.

A refinement of the invented method and apparatus additionally uses more than one receiver frequency band and employs spectral averaging to achieve reliable detection. A preferred apparatus uses a probe or a set of probes connected to a receiver tuned to 1.5 MHz and another probe or a set of probes connected to a separate receiver tuned to 2.5 MHz. The data received in the different frequency bands can then be summed. The summed data are then analyzed for substantial or called echoes. This increases the probability of defect detection because certain defects reflect some frequencies better than others and certain test specimen materials transmit some frequencies better than others. The efficiency of spectral averaging can be improved by obtaining both high and low frequency data in one scan. A simple form of spectral averaging can be realized by filtering the waveform received at a fixed probe position from a fixed direction into two or three frequency bands and adding the filtered waveforms for an improvement of defect detectability (test sensitivity).

Upon completing Mode I, a number of called echoes or calls indicating suspect defects will have been distinguished from the background interference. The locations of these suspect defects are recorded.

Each called echo must be confirmed. For this purpose, the Multiple-Beam Technique is used in its call-confirmation mode (Mode II). This operational mode is designed to reduce false alarming.

Mode II uses only probe A. The platform of this probe is inclined to produce a substantial longitudinal-wave component ($L_a$) which overlaps with its shear-wave component ($S_a$) in the regions of interest of the test specimen. The $S_a$ and $L_a$ pulses or signals are "associated", meaning that: (1) their sequence of arrival is independent of probe-to-defect distance and of test specimen composition; (2) the differences in their times-of-arrival are substantially independent of these factors; and (3) their relative amplitudes have a predictable relationship to each other as the probe is moved about the defect, a typical relationship being shown in FIG. 9.

Additionally, because the $S_a$ and $L_a$ pulses are produced by substantial defects, they are "durable" as opposed to echoes produced by coarse grains, material interfaces, and other minor test specimen inhomogeneities. Echoes that are substantially dependent upon array position are characterized as "easy-come-easy-go" echoes. Echoes that remain traceable regardless of minor changes in array position are durable.

The called echoes from Mode I are checked manually by the operator for durability and for the dissynchronous envelope pattern shown in FIG. 9.

FIG. 7 shows the use of multiple beams in the call-confirmation mode (Mode II) of the Multiple-Beam Technique. FIG. 8 shows various array positions upon the examination surface of an uncladded test specimen with regard to an ultrasonic wave reflector such as a crack-like defect upon the far surface of the test specimen. The $S_a$ and $L_a$ incident beams are shown emanating from the array at array position 6. The angle $\beta_1$ represents the direction of the incident shear beam with respect to a line perpendicular to the examination surface. The angle $gamma_1$ represents the direction of the incident longitudinal beam with respect to a line perpendicular to the examination surface. FIG. 9 shows the relative amplitudes of probe A's reflected shear pulse ($S_a$) and the associated reflected longitudinal pulse ($L_a$) returned by a crack-line defect upon a far surface being insonified by moving probe A as shown in FIG. 8. The array positions along the graph's horizontal axis correspond to the array positions shown in FIG. 8. The peak amplitude of the $S_a$ pulse is designed to be larger than that of the $L_a$ pulse because the shear pulse suffers a greater loss than the longitudinal pulse in propagating through a coarse-grained or bimetallic material [compare FIGS. 10(e) and 10(f)].

FIG. 10 shows the waveforms received when using only probe A in Mode II of the Multiple-Beam Technique as shown in FIG. 7. FIG. 10(a) shows a waveform received from a crack in an uncladded specimen when probe A is used and the described array is positioned at array position 9 as shown in FIGS. 8 and 9. At this position, the $S_a$ pulse is maximum. FIG. 10(b) shows a waveform received from a crack in a cladded test specimen when probe A is used and the described array is positioned at array position 9 as shown in FIGS. 8 and 9. At this position, the $S_a$ pulse is maximum. FIG. 10(c) shows a waveform received from a crack in an uncladded specimen when probe A is used and the described array is positioned at array position 3 as shown in FIGS. 8 and 9. At this position, the $L_a$ pulse is maximum. FIG. 10(d) shows a waveform received from a crack in an cladded specimen when probe A is used and the described array is positioned at array position 3 as shown in FIGS. 8 and 9. At this position, the $L_a$ pulse is maximum. FIG. 10(e) shows a waveform received from a crack in an uncladded specimen when probe A is used and the described array is positioned at array position 6 as shown in FIGS. 8 and 9. At this position, both the $S_a$ and $L_a$ pulses are substantial and neither is maximum. Comparison of the waveform of the uncladded test specimens shown in FIGS. 10(a), (b) and (c) show that the difference in time-of-arrival of the $S_a$ and $L_a$ pulses is practically independent of array position. FIG. 10(f) shows a waveform received from a crack in a cladded test specimen when probe A is used and the described array is positioned at array position 6 as shown in FIGS. 8 and 9. At this position, both the $S_a$ pulse and the $L_a$ pulse have been compromised to capture substantial $S_a$ and $L_a$ pulses in a single waveform. Comparison of the waveform received from the cladded test specimen of FIG. 10(f) with that received from the uncladded test specimen of FIG. 10(e) shows that the difference in time-of-arrival of the $S_a$ and $L_a$ pulses is practically independent of test specimen composition. Mode II uses this associated pulse pattern as part of the call-confirmation process.

The operator seeks the confirming, unique, dynamic and dissynchronous $S_a$-$L_a$ envelope pattern shown in FIG. 9 by judiciously moving probe A on the examination surface of the test specimen and aiming the overlapping beams at the region from which the call originated.

Figure 10F:
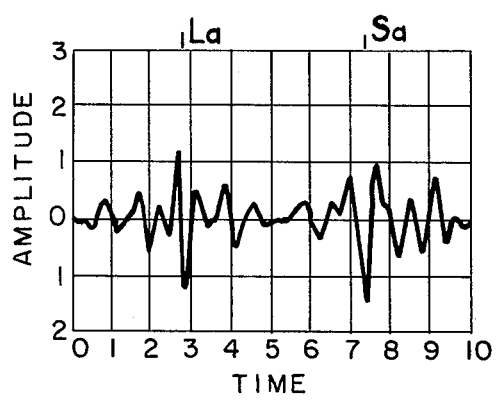

While moving probe A, the operator seeks the associated $L_a$ and $S_a$ pulses by observing whether called echo's are durable and whether any other echoes' amplitude rises and falls with the amplitude of the called echo in the dissynchronous manner shown in FIG. 9. The dissynchronous envelope pattern of FIG. 9 will appear for any crack-like defect breaking the test specimen's far surface. Because it uniquely and invariably characterizes such defects, the presence of the FIG. 9 $S_a$-$L_a$ associated pulse pair as shown in FIG. 10(f) confirms the presence of a crack-like defect breaking the far surface of the test specimen. Substantial echoes that do not behave dynamically as described by FIG. 9 for the $S_a$-$L_a$ associated pulse pair are interpreted as false calls.

Either Mode I or Mode II may be used separately to obtain useful data concerning possible defects. The data obtained by the invented method may be digitized at any step if desired. The methods of data collection described can be substantially duplicated with a single probe if the tests are performed in parts and the data stored for recombination. The Satellite-Pulse Techinque described in the applicant's prior filed U.S. patent application Ser. No. 142,216 can be used in connection with the Multiple-Beam Technique.

6. Summary

The basic problem to which the instant invention is directed is that cladded or coarse-grained metals cause statistical variations of great magnitude rendering the results of current nondestructive testing methods unreliable. The applicant has invented a device and a method that uses previously discarded data and previously unappreciated relationships which remain apparent in spite of the mass of spurious data obtained when testing these hard-to-inspect specimens. Waveform-averaging and pattern-recognition-based methods possessing sufficient redundancies to be reliable are used. Substantial independence from pulse amplitudes increases the power and versatility of the tool.

While the invention has been described in connection with the preferred embodiment, it is not intended to limit the invention to the particular forms set forth, but, on the contrary, it is intended to cover such alternatives, modifications, and equivalents as may be included within the spirit and scope of the invention as defined by the appended claims.

I claim:

1. An ultrasonic test method of detecting and confirming defects in a test specimen comprising:
   (a) detecting suspect defects by:
      (1) transmitting at least two detection beams of a same wave mode from a first set of multiple detection probe positions so that said two detection beams overlap in a region of interest in said test specimen;
      (2) receiving echoes of said two detection beams from said region of interest at a second set of multiple detection probe positions;
      (3) directionally averaging said echoes by means of a summing device to at least partially cancel at least some interference echoes and to reinforce at least some defect reflected echoes if a defect is present in said region of interest;
      (4) recording by means of a recording device substantial directionally averaged echoes as called echoes, said called echo indicating one or more suspect defects in said region of interest;
   (b) confirming suspect defects by:
      (1) transmitting at least two confirmation beams of different wave modes from at least one first confirmation probe position so at least two of said confirmation beams of said different wave modes overlap in said region of interest in said test specimen;
      (2) receiving echoes of said confirmation beams of said different wave modes from said region of interest at at least one second confirmation probe position;
      (3) moving said first confirmation probe position to move at least some of said confirmation beams of said different wave modes with respect to said region of interest to produce echoes having an associated reflected-pulse pattern if a defect is present in said region of interest;
      (4) recording by means of a recording device an associated reflected pulse pattern as confirming a suspect defect in said region of interest.

2. The ultrasonic test method of claim 1 additionally comprising calibrating a multiple-beam-angle device for use in said detecting and confirming operations, said multiple-beam-angle device comprised of at least one transmitting probe and at least one receiving probe, both said transmitting probe and said receiving probe being electrically connected to at least one ultrasonic test unit, said ultrasonic test unit comprising a transmitter, a receiver, and a resolution unit, comprising:
   first adjusting an amplitude recording level control means to achieve a signal-to-interference ratio that is large enough to allow signals to be distinguished from background interference;
   second adjusting said multiple-beam-angle device by adjusting detection probe positions to phase lock at least some detection beam signals; and
   third adjusting said multiple-beam-angle device to show time-of-arrival relationship of at least some confirmation beam signals.

3. The ultrasonic test method of claim 2 including a roof angle between a detection probe position A of said first set of multiple probe positions and a detection probe position B of said first set of multiple probe positions and additionally comprising:
   measuring the thickness of said test specimen; and
   using said test specimen thickness measurement to design said roof angle to cause said detection beams transmitted from said detection probe position A and said detection probe position B to significantly overlap in said region of interest and to yield a useful amplitude ratio between the resulting detection-beam signals.

4. The ultrasonic test method of claim 2 wherein an angle between said first confirmation probe position and an examination surface of said test specimen is an $\alpha_1$ angle and additionally comprising selecting said $\alpha_1$ angle sufficient to cause ultrasonic beams to refract sufficiently to create at least two confirmation beams of different wave modes, to cause at least two of said confirmation beams of said different wave modes to significantly overlap in said region of interest and to yield a useful pulse amplitude ratio between said confirmation beams of said different wave modes.

5. The ultrasonic test method of claim 4 wherein said first confirmation probe position and said second confirmation probe position are the same confirmation probe position.

6. The ultrasonic test method of claim 5 wherein said same confirmation probe position and a detection probe position are a same detection-confirmation probe position.

7. The ultrasonic test method of claim 5 additionally comprising selecting an $\alpha_1$ angle sufficient to cause refraction of said ultrasonic beams into a substantial shear-wave component and a substantial longitudinal-wave component, and to yield a shear-wave to longitudinal-wave component peak signal amplitude ratio in the range of 1:1 to 4:1.

8. The ultrasonic test method of claim 7 additionally comprising selecting an $\alpha_1$ angle to yield a shear-wave component to longitudinal-wave component peak signal amplitude ratio in the range of 2:1 to 3:1.

9. The ultrasonic test method of claim 7 additionally comprising adjusting a time scale upon said ultrasonic test unit so a distance between said longitudinal-wave and said shear-wave component signals is presented in the range of 20 percent to 80 percent of a time window of said ultrasonic test unit.

10. The ultrasonic test method of claim 7 additionally comprising transmitting by means of at least one damped unfocused probe detection beams and confirmation beams having pulse durations in the range of 0.5 to 5.0 cycles per pulse and having center frequencies in the range of 1.0 to 10 MHz.

11. The ultrasonic test method of claim 10 wherein said pulse durations are in the range of 0.5 to 1.5 cycles per pulse and said center frequencies are in the range of 1.5 to 3.0 MHz.

12. The ultrasonic test method of claim 5 additionally comprising designing said confirmation beams and said $\alpha_1$ angle such that said longitudinal-wave component is received prior to said shear-wave component and said shear-wave component is larger than said longitudinal wave component.

13. The ultrasonic test method of claim 5 additionally comprising moving said first confirmation probe position to move at least some of said confirmation beams with respect to said region of interest to determine echo durability, recording which of said echoes are durable, and only using said durable echoes in recording associated echoes.

14. An ultrasonic test method of detecting suspect defects in a region of interest in a test specimen comprising:
transmitting a first detection beam from a first transducer fixed at detection probe position A upon a shoe and a second detection beam from a second transducer fixed at a detection probe position B upon said shoe, said first transducer and said second transducer being approximately the same distance from said region of interest and, said detection probe position A and said detection probe position B having a roof angle sufficient to permit said detection beams to overlap in said region of interest in said test specimen;
receiving signals $S_a$ comprised of reflections from said first detection beam and signal $S_{ab}$ comprised of reflections from said second detection beam at said first transducer;
receiving signals $S_b$ comprised of reflections from said second detection beam and signals $S_{ba}$ comprised of reflections from said first detection beam at said second transducer;
cancelling some interference echoes and reinforcing some signals to produce an identifiable signal having a useful signal-to-interference ratio by summing said $S_a$, $S_b$, $S_{ab}$ and $S_{ba}$ signals in a summing device and by varying the spatial relationship of said transducers to said region of interest by moving said shoe.

15. The ultrasonic test method of claim 3 or 14 additionally comprising directionally averaging said echoes by means of a summing device that sums waveforms received at detection probe position A and detection probe position B to at least partially cancel at some interference echoes and to reinforce at least some defect reflected echoes due to the spatial separation between detection probe position A and detection probe position B.

16. The ultrasonic test method of claim 15 additionally comprising designing said roof angle to yield a detection probe position A detection-beam signal to detection probe position B detection-beam peak signal amplitude ratio in the range of 1:4 to 4:1.

17. The ultrasonic test method of claim 16 additionally comprising designing said roof angle to yield a detection probe position A detection-beam signal to detection probe position B detection-beam peak signal amplitude ratio in the range of 1:2 to 2:1.

18. The ultrasonic test method of claim 15 additionally comprising adjusting said first set of multiple detection probe position to examination surface angles to cause at least two of said detection beams to be transmitted within said test specimen with a substantial shear-wave beam component for test specimens of less than 20 mm thickness.

19. The ultrasonic test method of claim 15 additionally comprising adjusting said first set of multiple detection probe position to examination surface angles to create shear-wave beams as at least two of said detection beams in test specimens equal to or greater than 20 mm thickness or more.

20. The ultrasonic test method of claim 15 additionally comprising transmitting said detection beams of more than one center frequency from said first set of multiple detection probes to increase reliability of the method through increased redundancy.

21. The ultrasonic test method of claim 20 additionally comprising filtering a waveform received from said more than one center frequency detection beams into frequency bands by means of a waveform frequency filtering unit and adding said filtered waveforms by means of a resolution unit to improve sensitivity of said ultrasonic test method to defects.

22. The ultrasonic test method of claim 15 wherein said substantial directionally averaged echoes are any echoes whose amplitude exceeds twice the mean amplitude of the interference echoes.

23. The ultrasonic test method of claim 15 wherein said first set of multiple detection probe positions and said second set of multiple detection probe positions are the same set of multiple probe positions.

24. The ultrasonic test method of claim 15 wherein said first set of multiple detection probe positions and said second set of multiple detection probe positions are a same set of multiple detection probe positions.

25. An ultrasonic test method of confirming suspect defects in a test specimen comprising:
transmitting at least two confirmation beams of different wave modes from at least one first confirmation probe position so at least two of said confirmation beams of said different wave modes overlap in said region of interest in said test specimen;
receiving echoes of said confirmation beams of said different wave modes from said region of interest at at least one second confirmation probe position;
moving said first confirmation probe position to move at least some of said confirmation beams of said different wave modes with respect to said region of interest to produce echoes having an associated reflected-pulse pattern if a defect is present in said region of interest;
recording by means of a recording device an associated reflected pulse pattern as confirming a suspect defect in said region of interest.

26. A multiple-beam-angle device for detecting and confirming a defect within a test specimen comprising:
at least one wedge capable of being placed upon said test specimen to conduct acoustical waves, said wedge having at least two platforms for locating probes a platform A and a platform B, a roof angle between platform A and platform B, and an $\alpha_1$ angle between platform A and an examination surface of said test specimen;
at least two probes with at least one of said probes located upon each of said platforms;
at least one ultrasonic test unit connected electrically to said two probes, said ultrasonic test unit comprising a transmitter, a receiver, and a resolution unit;
said roof angle being sufficient to cause detection beams of the same wave mode transmitted from said two probe positions to significantly overlap in a region of interest in said test specimen and to yield a useful amplitude ratio between resulting detection beam signals;
said $\alpha_1$ angle being sufficient to cause an ultrasonic beam from said probe located upon platform A to refract sufficiently to create at least two substantial confirmation beams of different wave modes, to cause said two substantial confirmation beams of said different wave modes to significantly overlap in said region of interest and to yield a useful amplitude ratio between resulting confirmation beams signals.

27. The multiple-beam-angle device of claim 26 wherein said probes are unfocused probes and said wedge is damped, said device is capable of transmitting pulse durations within the range of 0.5 to 5.0 cycles per pulse and is capable of transmitting center frequencies in the range of 1.0 to 10 MHz.

28. The multiple-beam-angle device of claim 27 wherein said $\alpha_1$ angle is in the range of 0° to 29° for causing said ultrasonic beam from said probe located on platform A to refract into a substantial longitudinal-wave and a substantial shear-wave.

29. The multiple-beam-angle device of claim 28 wherein said $\alpha_1$ angle is in the range of 22° to 27°.

30. The multiple-beam-angle device of claim 28 wherein said roof angle is in the range of 6° to 12° for causing said detection beams to significantly overlap in said region of interest.

31. The multiple-beam-angle device of claim 28 wherein said probes are adjustably fixed upon said platforms to permit said probes to be interchangeably adjusted upon said platforms and fixed upon said platforms for phase locking of at least some of said resulting detection beam signals.

32. The multiple-beam-angle device of claim 31 wherein said device is capable of transmitting more than one center frequency band, capable of filtering received waveforms into different filtered waveforms, and capable of summing said different filtered waveforms for spectral averaging of said filtered waveforms.

33. A method of calibrating a multiple-beam angle device to phase lock detection signals of the same wave mode and to display confirmation signals of different wave mode comprised of:
transmitting two detections beams into a test specimen, a first detection beam from a first transducer fixed at detection probe position A and a second detection beam from a second transducer fixed at a detection probe position B, said detection probe position A and said detection probe position B being located upon a shoe and having a roof angle between them sufficient to permit said detection beams to significantly overlap in a region of interest in said test specimen;
receiving detection signals comprised of reflections from said first detection beam and signals comprised of reflections from said second detection beam at said first transducer;
receiving detection signals comprised of reflections from said second detection beam and signals comprised of reflections from said first detection beam at said second transducer;
phase locking said detection signals by adjusting the position of said transducers upon their platforms relative to each other to maximize the degree of overlap between said detection signals as displayed upon said resolution unit;
identifying said phase locked combination of said detection signals;
adjusting an amplitude recording level control means to produce a useful phase locked detection signal-to-interference ratio;
transmitting confirmation beams of different wave mode from one of said transducers into said test specimen;
receiving at least two confirmation signals of different wave mode comprised of reflections from said confirmation beams at said confirmation beam transducer;
identifying said confirmation signals of different wave mode and adjusting a resolution unit's time scale to simultaneously display both said confirmation signals of different wave mode.

* * * * *